United States Patent
Rahbar et al.

(12)

(10) Patent No.: US 6,337,350 B1
(45) Date of Patent: Jan. 8, 2002

(54) INHIBITORS OF FORMATION OF ADVANCED GLYCATION ENDPRODUCTS (AGES)

(75) Inventors: Samuel Rahbar, Encino, CA (US); Iraj Lalezari, Scarsdale, NY (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/543,703

(22) Filed: Apr. 5, 2000

Related U.S. Application Data

(60) Provisional application No. 60/127,835, filed on Apr. 5, 1999.

(51) Int. Cl.⁷ .................. A61K 31/40; A61K 35/14; A61K 38/16; A61P 31/10; C07C 69/76
(52) U.S. Cl. .................. 514/596; 514/601; 560/1; 560/8; 560/18; 560/27; 560/34; 560/53; 562/425; 562/426; 562/439; 562/440; 562/452; 562/455; 546/257; 549/29; 549/229
(58) Field of Search .................. 560/1, 8, 18, 27, 560/34, 53, 64; 562/425, 426, 439, 440, 452, 455; 514/596, 601; 544/106, 285; 546/257; 549/29, 229

(56) References Cited

U.S. PATENT DOCUMENTS

| | | | |
|---|---|---|---|
| 4,661,579 A | 4/1987 | Blöcker | 528/170 |
| 4,921,997 A | 5/1990 | Lalezari et al. | 560/34 |
| 5,093,367 A | 3/1992 | Lalezari et al. | 514/564 |
| 5,268,500 A | 12/1993 | Lalezari et al. | 560/34 |
| 5,272,176 A * | 12/1993 | Ulrich et al. | 514/535 |
| 5,292,935 A | 3/1994 | Lalezari et al. | 562/439 |
| 5,602,277 A | 2/1997 | Babu et al. | 562/439 |
| 5,677,330 A * | 10/1997 | Abraham et al. | 548/403 |
| 5,716,987 A | 2/1998 | Wille | 514/543 |
| 5,962,651 A * | 10/1999 | LaleZari et al. | 530/385 |

FOREIGN PATENT DOCUMENTS

| WO | WO95/31192 | 11/1995 |
|---|---|---|

OTHER PUBLICATIONS

J.M. Calatayud, "Favorable Effects of the Lipid–Lowering and Platelet Antiaggregant Plafibride on the Aging Process of Mice of the C57BL/6J Strain," Meth and Find Exptl. Clin Pharmacol 5(10):707–714, 1983.

S. Rahbar et al., "A new rapid method to detect inhibition of Amadori product generated by δ–gluconolactone," Clinical Chimica Acta 287:123–130, 1999.

S. Rahbar et al., "Novel Inhibitors of Advanced Glycation Endproducts," Biochemical and Biophysical Research Communications 262:651–656, 1999.

The Merck Index, paragraphs 462, 1927 and 4857, 1996.

Lalezari et al. J. Med. Chem., 32, 2352–2357, 1989.*

Aldirch catalog 3,8,786,805, 1994–1995.*

* cited by examiner

*Primary Examiner*—Richard L. Raymond
*Assistant Examiner*—Venkataraman Balasubramanian
(74) *Attorney, Agent, or Firm*—Rothwell, Figg, Ernst & Manbeck

(57) ABSTRACT

Derivatives of aryl and heterocyclic ureido and aryl and heterocyclic carboxamido phenoxy isobutyric acids have been found to inhibit the nonenzymatic glycation of proteins which often results in formation of advanced glycation endproducts and crosslinks. Many other phenoxyisobutyric acid derivatives as well as certain other compounds as set out in this disclosure also have been found to inhibit the nonenzymatic glycation of proteins. The nonenzymatic glycation and crosslinking of proteins is a part of the aging process with the glycation endproducts and crosslinking of long-lived proteins increasing with age. This process is increased at elevated concentrations of reducing sugars in the blood and in the intracellular environment such as occurs with diabetes. The structural and functional integrity of the affected molecules become perturbed by these modifications and can result in severe consequences. The compounds of the present invention can be used to inhibit this process of nonenzymatic glycation and therefore to inhibit some of the ill effects caused by diabetes or by aging. The compounds are also useful for preventing premature aging, spoilage of proteins in food and can prevent discoloration of teeth.

22 Claims, 11 Drawing Sheets

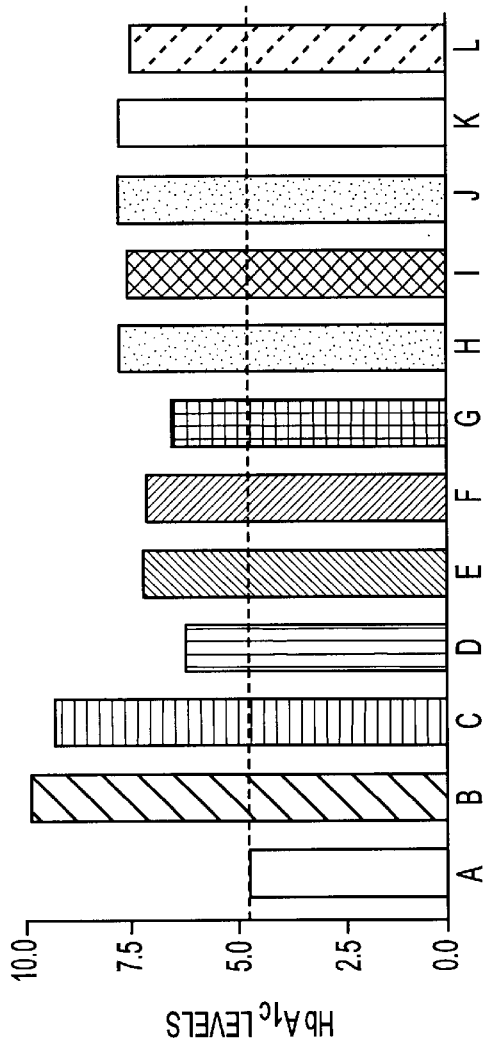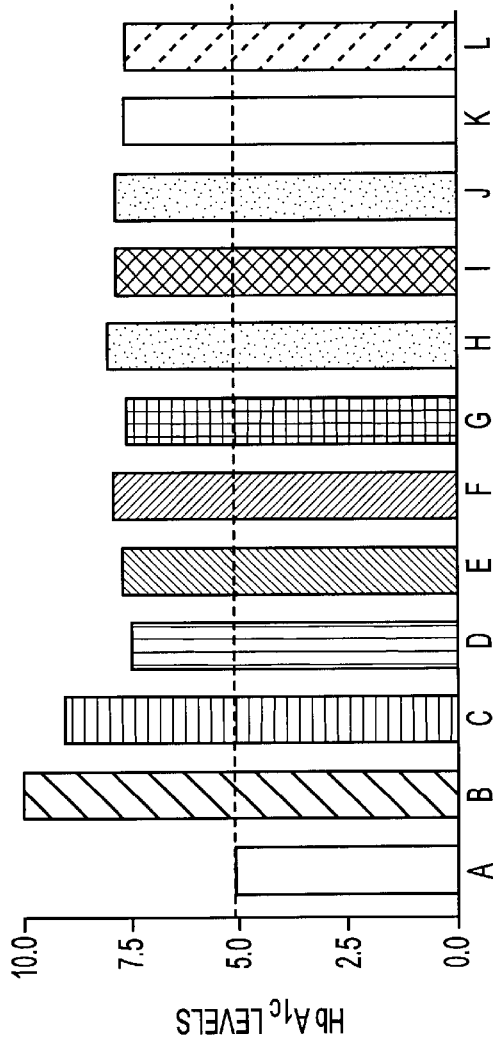

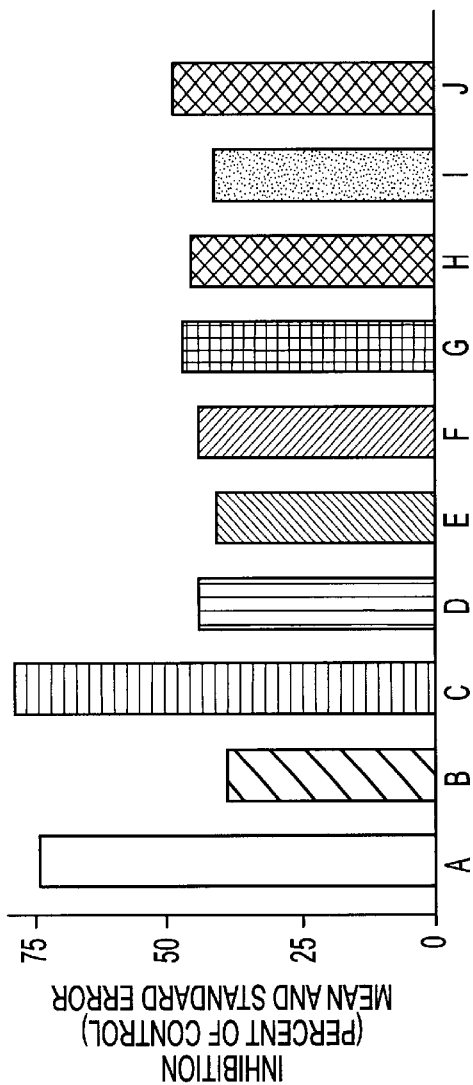
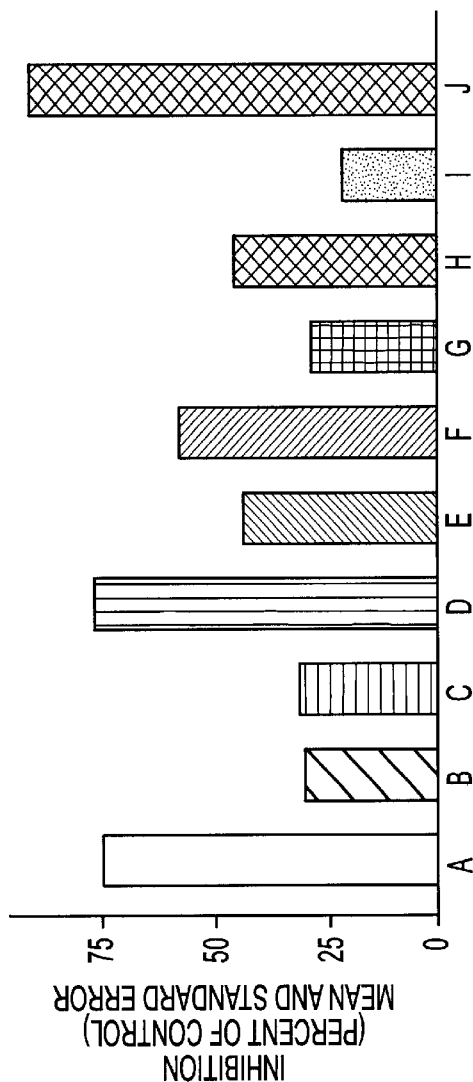
FIG. 3A
FIG. 3B

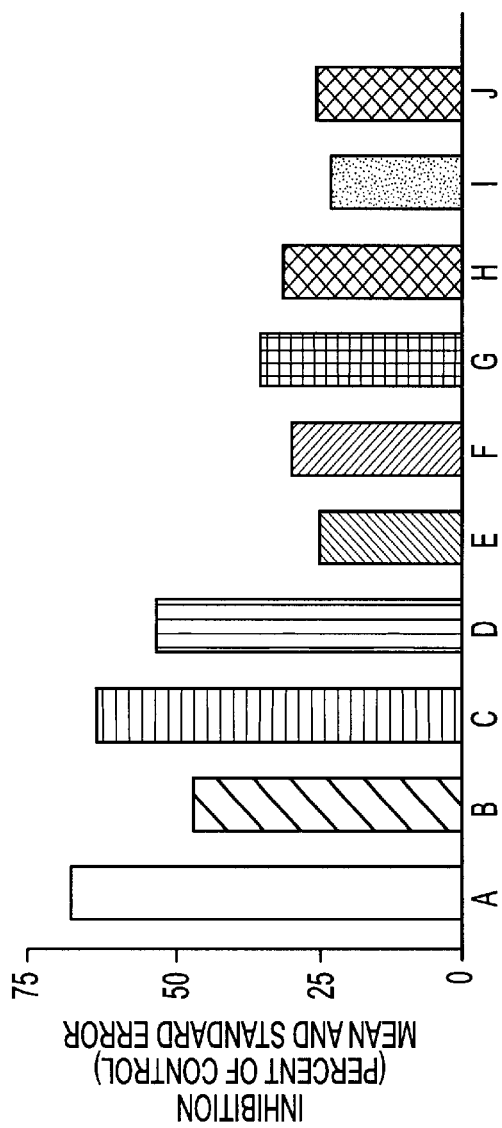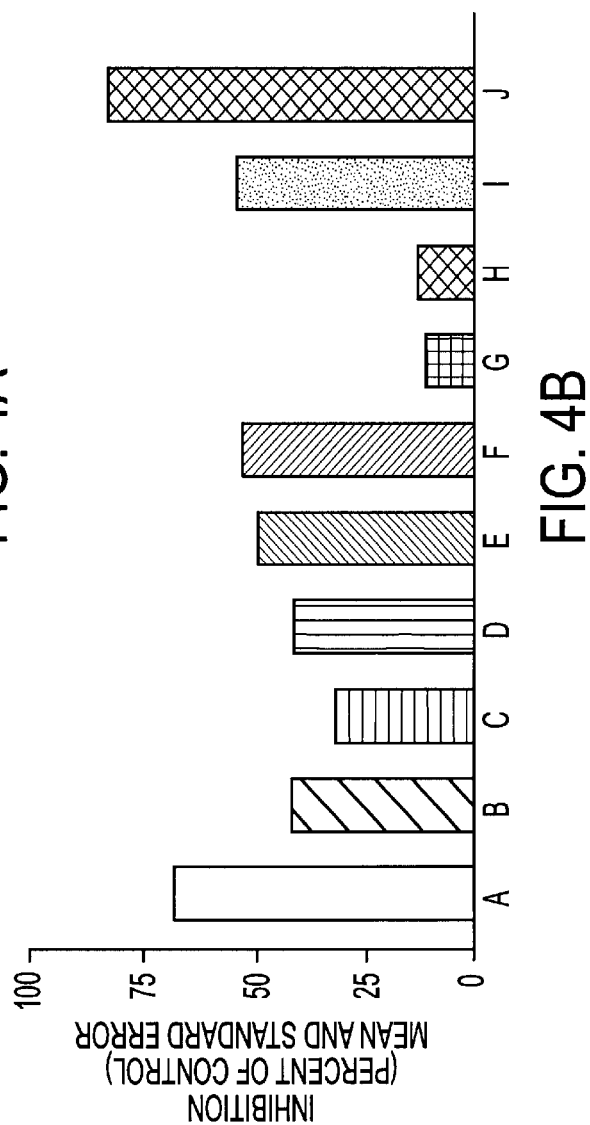

INHIBITORS OF FORMATION OF ADVANCED GLYCATION ENDPRODUCTS (AGES)

CROSS-REFERENCE TO RELATED APPLICATION

This application is related to provisional application Serial No. 60/127,835, filed Apr. 5, 1999, which is incorporated herein by reference.

BACKGROUND OF THE INVENTION

The present invention relates generally to the modification and aging of proteins through reaction with glucose and other reducing sugars, such as fructose or ribose and more particularly to the inhibition of nonenzymatic glycation of proteins which often results in formation of advanced glycation endproducts and crosslinks.

An elevated concentration of reducing sugars in the blood and in the intracellular environment results in the nonenzymatic formation of glycation and dehydration condensation complexes known as advanced glycation end-products (AGE's). These complex products form on free amino groups on proteins, on lipids and on DNA (Bucala and Cerami, 1992; Bucala et al., 1993; Bucala et al., 1984). This phenomenon is called "browning" or "Maillard" reaction and was discovered early in this century by the food industry (Maillard, 1916). The significance of a similar process in biology became evident only after the discovery of the glycosylated hemoglobins and their increased presence in diabetic patients (Rahbar, 1968; Rahbar et al., 1969). In human diabetic patients and in animal models of diabetes, these nonenzymatic reactions are accelerated and cause increased AGE formation and increased glycation of long-lived proteins such as collagen, fibronectin, tubulin, lens crystallin, myelin, laminin and actin, in addition to hemoglobin and albumin, and also of LDL associated lipids and apoprotein. Moreover, brown pigments with spectral and fluorescent properties similar to those of late-stage Maillard products have also been found in vivo in association with several long-lived proteins such as lens crystallin proteins and collagen from aged individuals. An age-related linear increase in pigments was observed in human dura collagen between the ages of 20 to 90 years. AGE modified proteins increase slowly with aging and are thought to contribute to normal tissue remodeling. Their level increases markedly in diabetic patients as a result of sustained high blood sugar levels and lead to tissue damage through a variety of mechanisms including alteration of tissue protein structure and function, stimulation of cellular responses through AGE specific receptors or the generation of reactive oxygen species (ROS) (for a recent review see Boel et al., 1995). The structural and functional integrity of the affected molecules, which often have major roles in cellular functions, become perturbed by these modifications, with severe consequences on affected organs such as kidney, eye, nerve, and micro-vascular functions (Silbiger et al., 1993; Brownlee et al., 1985).

Structural changes on macromolecules by AGE's are known to accumulate under normal circumstances with increasing age. This accumulation is severely accelerated by diabetes and is strongly associated with hyperglycemia. For example, formation of AGE on protein in the subendothelial basement membrane causes extensive cross-link formation which leads to severe structural and functional changes in protein/protein and protein/cell interaction in the vascular wall (Haitoglou et al., 1992; Airaksinen et al., 1993).

Enhanced formation and accumulation of advanced glycation end products (AGE's) have been proposed to play a major role in the pathogenesis of diabetic complications and in aging, leading to progressive and irreversible intermolecular protein crosslinkings (Monnier et al., 1986). This process is accelerated by diabetes and has been postulated to contribute to the development of a range of diabetic complications including nephropathy (Nicholls and Mandel, 1989), retinopathy (Hammes et al., 1991) and neuropathy (Cameron et al., 1992). Particularly, tissue damage to the kidney by AGE's leads to progressive decline in renal function and end-stage renal disease (ESRD) (Makita et al., 1994), and accumulation of low-molecular-weight (LMW) AGE peptides (glycotoxins) (Koschinsky et al., 1997) in the serum of patients with ESRD (Makita et al., 1991). These low molecular weight (LMW)-AGE's can readily form new crosslinks with plasma or tissue components, e.g., low density lipoprotein (LDL) (Bucala et al., 1994) or collagen (Miyata et al., 1993) and accelerate the progression of tissue damage and morbidity in diabetics.

Direct evidence indicating the contribution of AGE's in the progression of diabetic nephropathy has recently been reported (Vlassara et al., 1994). Indeed, the infusion of preformed AGE's into healthy rats induces glomerular hypertrophy and mesangial sclerosis, gene expression of matrix proteins and production of growth factors (Brownlee et al., 1991; Vlassara et al., 1995). Further studies have revealed that aminoguanidine (AG), an inhibitor of AGE formation, ameliorates tissue impairment of glomeruli and reduces albuminuria in induced diabetic rats (Soulis-Liparota et al., 1991; Itakura et al., 1991). In humans, decreased levels of hemoglobin (Hb)-AGE (Makita et al., 1992) concomitant with amelioration of kidney function as the result of aminoguanidine therapy in diabetic patients, provided more evidence for the importance of AGE's in the pathogenesis of diabetic complications (Bucala and Vlassara, 1997).

The global prevalence of diabetes mellitus, in particular in the United States, afflicting millions of individuals with significant increases of morbidity and mortality, together with the great financial burden for the treatment of diabetic complications in this country, are major incentives to search for and develop drugs with a potential of preventing or treating complications of the disease. So far the mechanisms of hyperglycemia-induced tissue damage in diabetes are not well understood. However, four pathogenic mechanisms have been proposed, including increased polyol pathway activity, activation of specific protein kinase C (PKC) isoforms, formation and accumulation of advanced glycation endproducts, and increased generation of reactive oxygen species (ROS) (Kennedy and Lyons, 1997). Most recent immunohistochemical studies on different tissues from kidneys obtained from ESRD patients (Horie et al., 1997) and diabetic rat lenses (Matsumoto et al., 1997), by using specific antibodies against carboxymethyllysine (CML), pentosidine, the two known glycoxidation products and pyrraline, have localized these AGE components in different lesions of the kidneys and the rat lens, and have provided more evidence in favor of protein-AGE formation in close association with generation of ROS to be major factors in causing permanent and irreversible modification of tissue proteins. Therefore, inhibitors of AGE formation and antioxidants hold promise as effective means of prevention and treatment of diabetic complications.

In addition to aging and diabetes, the formation of AGEs has been linked with several other pathological conditions. IgM anti-IgG-AGE appears to be associated with clinical measurements of rheumatoid arthritis activity (Lucey et al., 2000). A correlation between AGEs and rheumatoid arthritis was also made in North American Indians (Newkirk et al., 1998). AGEs are present in brain plaques in Alzheimer's disease and the presence of AGEs may help promote the development of Alzheimer's disease (Durany et al., 1999; Munch et al., 1998; Munch et al., 1997). Uremic patients have elevated levels of serum AGEs compared to age-matched controls (Odani et al., 1999; Dawnay and Millar, 1998). AGEs have also been correlated with neurotoxicity (Kikuchi et al., 1999). AGE proteins have been associated with atherosclerosis in mice (Sano et al., 1999) and with atherosclerosis in persons undergoing hemodialysis (Takayama et al., 1998). A study in which aminoguanidine was fed to rabbits showed that increasing amounts of aminoguanidine led to reduced plaque formation in the aorta thus suggesting that advanced glycation may participate in atherogenesis and raising the possibility that inhibitors of advanced glycation may retard the process (Panagiotopoulos et al., 1998). Significant deposition of N(epsilon)-carboxymethyl lysine (CML), an advanced glycation endproduct, is seen in astrocytic hyaline inclusions in persons with familial amyotrophic lateral sclerosis but is not seen in normal control samples (Kato et al., 1999; Shibata et al., 1999). Cigarette smoking has also been linked to increased accumulation of AGEs on plasma low density lipoprotein, structural proteins in the vascular wall, and the lens proteins of the eye, with some of these effects possibly leading to pathogenesis of atherosclerosis and other diseases associated with tobacco usage (Nicholl and Bucala, 1998). Finally, a study in which aminoguanidine was fed to rats showed that the treatment protected against progressive cardiovascular and renal decline (Li et al., 1996).

The mechanism of the inhibitory effects of aminoguanidine in the cascade of glycosylation events has been investigated. To date, the exact mechanism of AG-mediated inhibition of AGE formation is not completely known. Several lines of in vitro experiments resulted in contrasting conclusions. Briefly, elevated concentrations of reducing sugars cause spontaneous reactions between carbohydrate carbonyl and protein amino groups leading to:

1. Reversible formation of Schiff's bases followed by
2. Amadori condensation/dehydration products such as 3-deoxyglucason (3-DG), a highly reactive dicarbonyl compound (Kato et al., 1990).
3. Irreversible and highly reactive advanced glycosylation endproducts. Examples of early Amadori products are ketoamines which undergo further condensation reactions to form late AGE's. A number of AGE products have been purified and characterized recently, each one constituting only minor fractions of the in vivo generated AGE's. Examples are pyrraline, pentosidine, carboxymethyl-lysine (CML), carboxyethyl-lysine (CEL), crossline, pyrrolopyridinium, methylglyoxal lysine dimer (MOLD), Arg-Lys imidazole, arginine pyridinium, cypentodine, piperidinedinone enol and alkyl, formyl, diglycosyl-pyrrole (Vlassara, 1994).

Analysis of glycation products formed in vitro on a synthetic peptide has demonstrated that aminoguanidine does not inhibit formation of early Amadori products (Edelstein and Brownlee, 1992). Similar conclusions were reached by analysis of glycation products formed on BSA (Requena et al., 1993). In both experiments AGE formation was strongly inhibited by AG as analyzed by fluorescence measurements and by mass spectral analysis. The mass spectral analysis did not detect peptide complexes with molecular mass corresponding to an incorporation of AG in the complex. Detailed mechanistic studies using NMR, mass spectroscopy and X-ray diffraction have shown that aminoguanidine reacts with AGE precursor 3-DG to form 3-amino-5- and 3-amino-6-substituted triazines (Hirsch et al., 1992). In contrast, other experiments using labeled $^{14}$C-AG with lens proteins suggest that AG becomes bound to the proteins and also reacts with the active aldose form of free sugars (Harding, 1990).

Several other potential drug candidates as AGE inhibitors have been reported recently. These studies evaluated the agent's ability to inhibit AGE formation and AGE-protein crosslinking compared to that of aminoguanidine (AG) through in vitro and in vivo evaluations (Nakamura et al., 1997; Kochakian et al., 1996). A recent breakthrough in this field is the discovery of a compound, N-phenacylthiazolium bromide (PTB), which selectively cleaves AGE-derived protein crosslinks in vitro and in vivo (Vasan et al., 1996; Ulrich and Zhang, 1997). The pharmacological ability to break irreversible AGE-mediated protein crosslinking offers potential therapeutic use.

It is well documented that early pharmaceutical intervention against the long-term consequences of hyperglycemia-induced crosslinking, prevent the development of severe late complications of diabetes. The development of nontoxic and highly effective drugs that completely stop glucose-mediated crosslinking in the tissues and body fluids is a highly desirable goal. The prototype of the pharmaceutical compounds investigated both in vitro and in vivo to intervene with the formation of AGE's on proteins is aminoguanidine (AG), a small hydrazine-like compound (Brownlee et al., 1986). However, a number of other compounds were found to have such an inhibitory effect on AGE formation. Examples are D-lysine (Sensi et al., 1993), desferrioxamine (Takagi et al., 1995), D-penicillamine (McPherson et al., 1988), thiamine pyrophosphate and pyridoxamine (Booth et al., 1997) which have no structural similarities to aminoguanidine.

Clinical trials of AG as the first drug candidate intended to inhibit AGE formation are in progress (Corbett et al., 1992). A number of hydrazine-like and non-hydrazine compounds have been investigated. So far AG has been found to be the most useful with fewer side effects than other tested compounds of the prior art. However, AG is a well known selective inhibitor of nitric oxide (NO) and can also have antioxidant effects (Tilton et al., 1993).

A number of other potential drug candidates to be used as AGE inhibitors have been discovered recently and evaluated both in vitro and in vivo (Nakamura et al., 1997; Soulis et al., 1997). While the success in studies with aminoguanidine and similar compounds is promising, the need to develop additional inhibitors of AGEs continues to exist in order to broaden the availability and the scope of this activity and therapeutic utility.

SUMMARY OF THE INVENTION

Derivatives of aryl and heterocyclic ureido and aryl and heterocyclic carboxarnido phenoxyisobutyric acids and of benzoic acid have been found to inhibit the nonenzymatic glycation of proteins which often results in formation of advanced glycation endproducts and crosslinks. Many other phenoxyisobutyric acid derivatives as well as certain other compounds as set out below also have been found to inhibit the nonenzymatic glycation of proteins. The nonenzymatic glycation and crosslinking of proteins is a part of the aging process with the glycation endproducts and crosslinking of long-lived proteins increasing with age. This process is increased at elevated concentrations of reducing sugars in the blood and in the intracellular environment such as occurs with diabetes. The structural and functional integrity of the affected molecules become perturbed by these modifications and can result in severe consequences. The compounds of the present invention can be used to inhibit this process of nonenzymatic glycation and crosslinking and therefore to inhibit some of the ill effects caused by diabetes or by aging. The compounds are also useful for preventing premature aging, rheumatoid arthritis, Alzheimer's disease, uremia, neurotoxicity, atherosclerosis, and spoilage of proteins in food and can prevent discoloration of teeth.

BRIEF DESCRIPTION OF THE FIGURES

FIGS. 2A–B show the effects of various inhibitor compounds on whole blood incubated for 5 hours (FIG. 2A) or 16 hours (FIG. 2B) with δ-Glu. The bars of the graph represent the $HbA_{1C}$ levels obtained. The inhibitors were used at 1 mM final concentrations except for aminoguanidine which was at 50 mM. For FIG. 2A the bars of the graph are: A: baseline control which contains blood and PBS but no δ-Glu; B: contains δ-Glu treated blood with no inhibitor present; C: contains blood plus δ-Glu plus aminoguanidine; D-L: these contain blood plus δ-Glu plus LR26, LR28, LR29, LR33, LR36, LR41, LR45, LR49 and LR62, respectively For FIG. 2B the bars of the graph are: A: baseline control which contains blood and PBS but no δ-Glu; B: contains δ-Glu treated blood with no inhibitor present; C: contains blood plus δ-Glu plus aminoguanidine; D-L: these contain blood plus δ-Glu plus LR66, LR67, LR71, LR79, LR80, LR81, LR85, LR88 and LR92, respectively. All samples contain the same concentration of blood and δ-Glu.

FIGS. 3A–B demonstrate the data from a BSA-glucose assay and shows the percent inhibition of AGE formation by 1 mM of inhibitors as compared to 50 mM aminoguanidine. For FIG. 3A the bars of the graph are: A: aminoguanidine; B: LR26, C: LR28, D: LR29, E: LR33, F: LR36, G: LR41, H: LR45, I: LR49 and J: LR62. For FIG. 3B the bars of the graph are: A: aminoguanidine; B: LR66, C: LR67, D: LR71, E: LR79, F: LR80, G: LR81, H: LR85, I: LR88 and J: LR92.

FIGS. 4A–B present the data from a G.K.-ribose assay and shows the percent inhibition of AGE formation by 1 mM of inhibitors as compared to 50 mM aminoguanidine. For FIG. 4A the bars of the graph represent: A: aminoguanidine, B: LR26, C: LR28, D: LR29, E: LR33, F: LR36, G: LR41; H: LR45, I: LR49 and J: LR62. For FIG. 4B the bars of the graph represent: A: aminoguanidine, B: LR66, C: LR67, D: LR71, E: LR79, F: LR80, G: LR81, H: LR85, I: LR88 and J: LR92.

DETAILED DESCRIPTION OF THE INVENTION

In the course of screening different classes of organic compounds for investigation of their possible inhibitory effects on advanced glycation endproducts (AGE's), we found that most of the phenylureido substituted phenoxy propionic acid derivatives tested have inhibitory effects and several of these compounds were potent inhibitors of AGE-formation at concentrations much lower than an equally inhibiting concentration of aminoguanidine.

The compounds and their useful compositions utilized in the present invention contain agents capable of reacting with the highly active carbonyl intermediate of an early glycation product thereby preventing those early products from later forming the advanced glycation endproducts which lead to protein crosslinking and to protein aging.

Other utilities envisioned for the present invention are: prevention of premature aging and of spoilage of the proteins in foodstuffs. The present agents are also useful in the area of oral hygiene as they prevent discoloration of teeth.

Compounds

Figure 1:
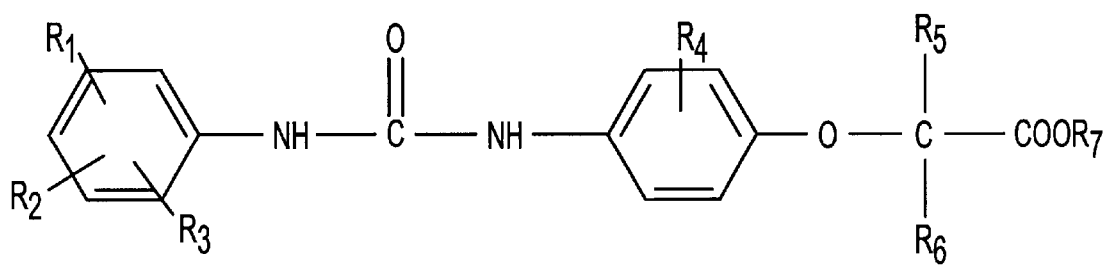
FIG. 1 represents a general formula encompassing many but not all of the aryl and heterocyclic ureido and aryl and heterocyclic carboxamido phenoxyisobutyric acids of the invention. $R_1$, $R_2$, $R_3$ and $R_4$ may be the same or different and are independently selected from the group consisting of hydrogen, halogen, straight or branched chain alkyl of from 1–6 carbon atoms, aryl, cycloalkyl of 3 to 7 carbon atoms, and alkoxy of 1 to 6 carbon atoms; $R_5$ and $R_6$ may be the same or different and are selected from the group consisting of hydrogen, halogen, straight or branched chain alkyl groups of from 1 to 6 carbon atoms, aralkyl wherein the alkyl portion has from 1 to 6 carbon atoms, cycloalkyl of from 3 to 7 carbon atoms and aryl; and $R_7$ is hydrogen or a straight or branched chain alkyl group of 1 to 6 carbon atoms.
Figure 5:
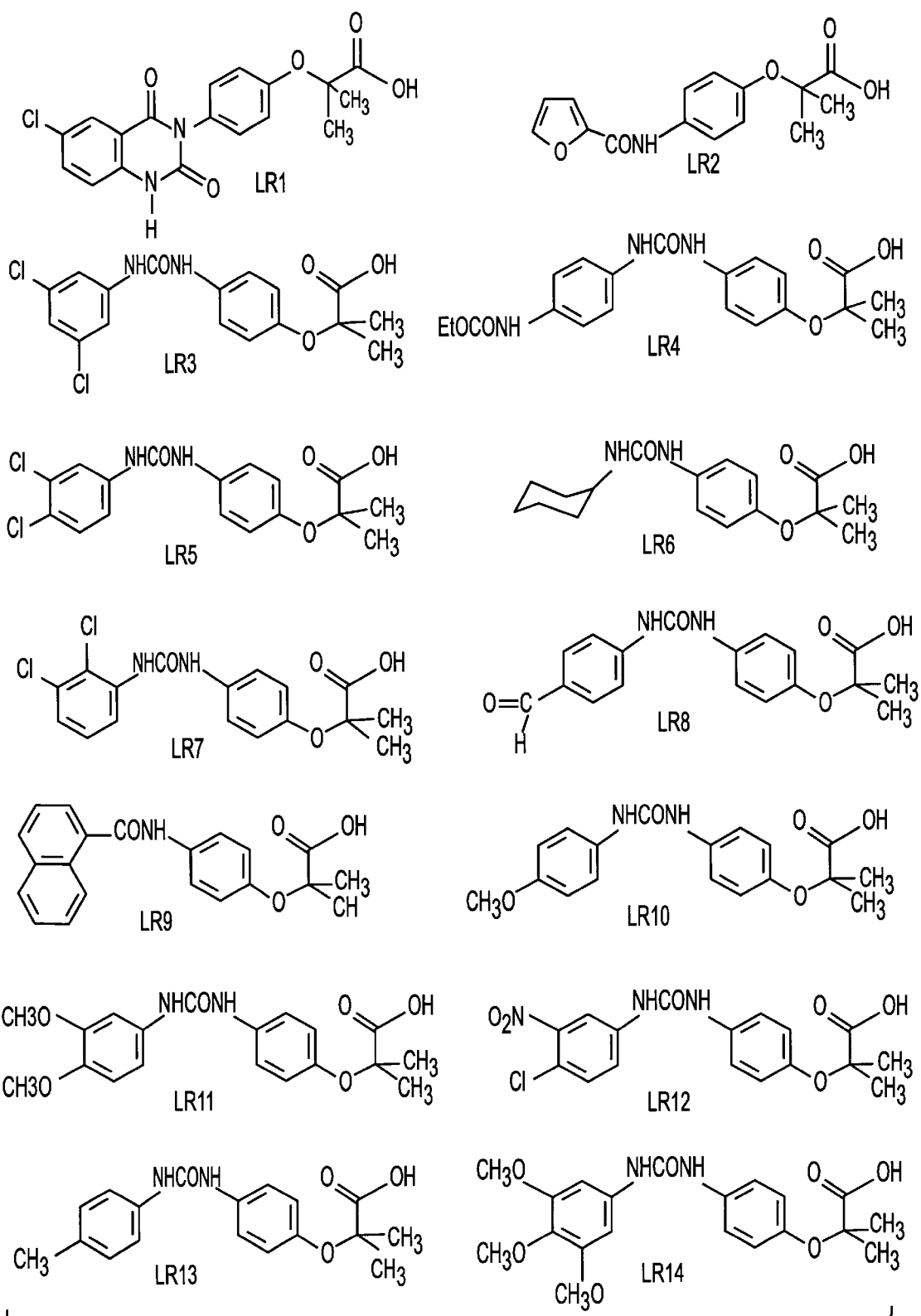
FIG. 5 shows the structures of LR1–LR14.
Figure 6:
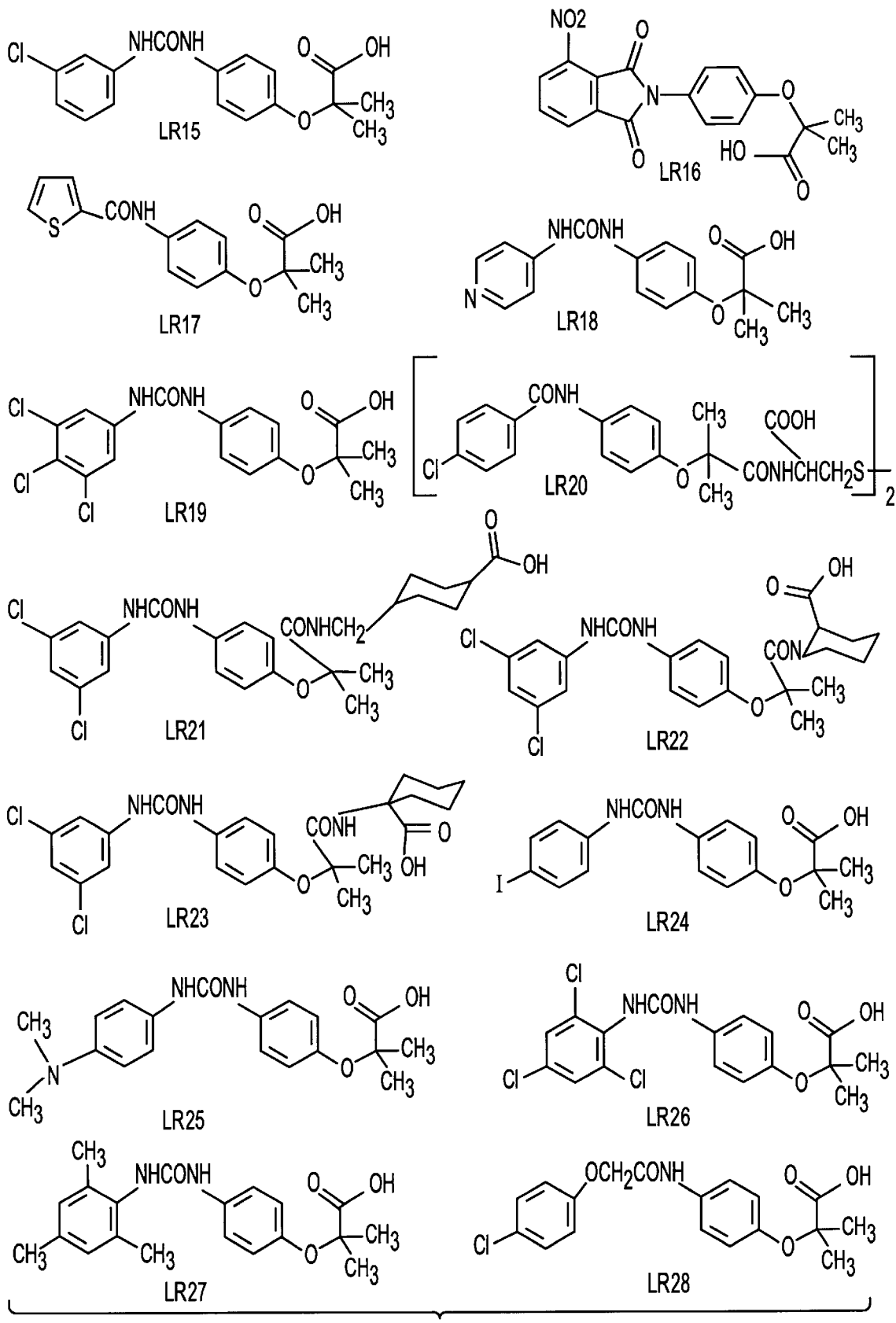
FIG. 6 shows the structures of LR15–LR28.
Figure 7:
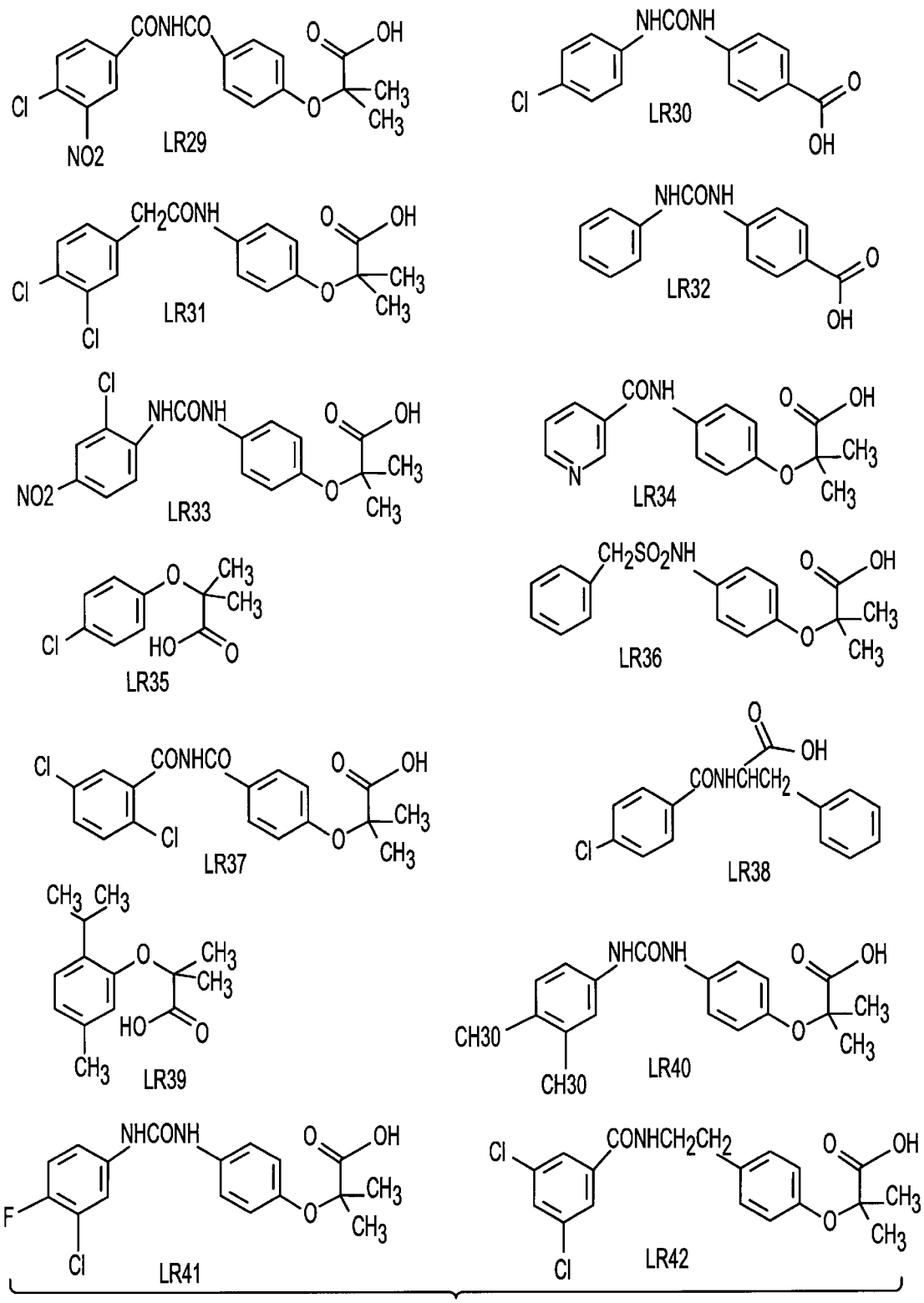
FIG. 7 shows the structures of LR29–LR42.
Figure 8:
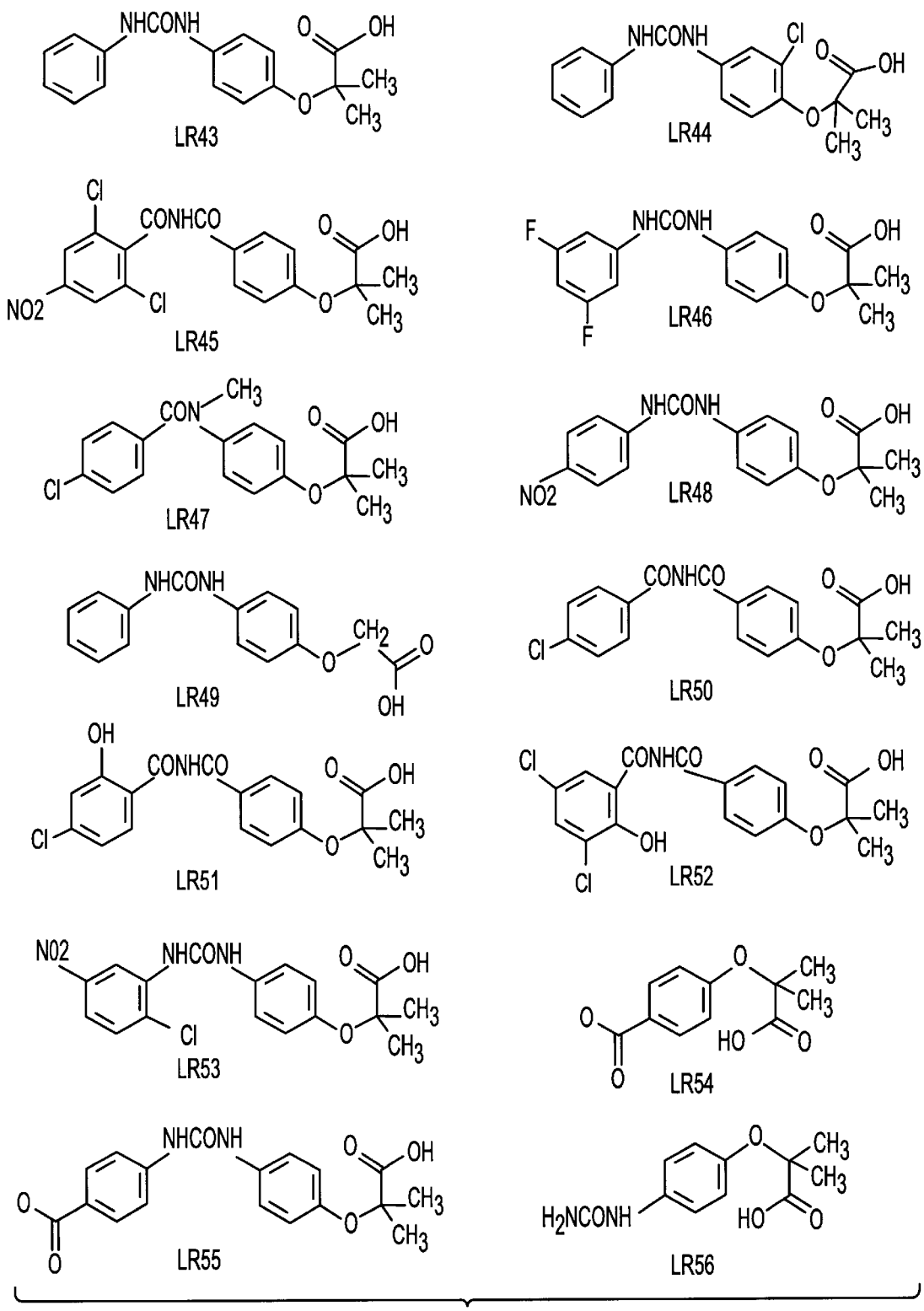
FIG. 8 shows the structures of LR43–LR56.
Figure 9:
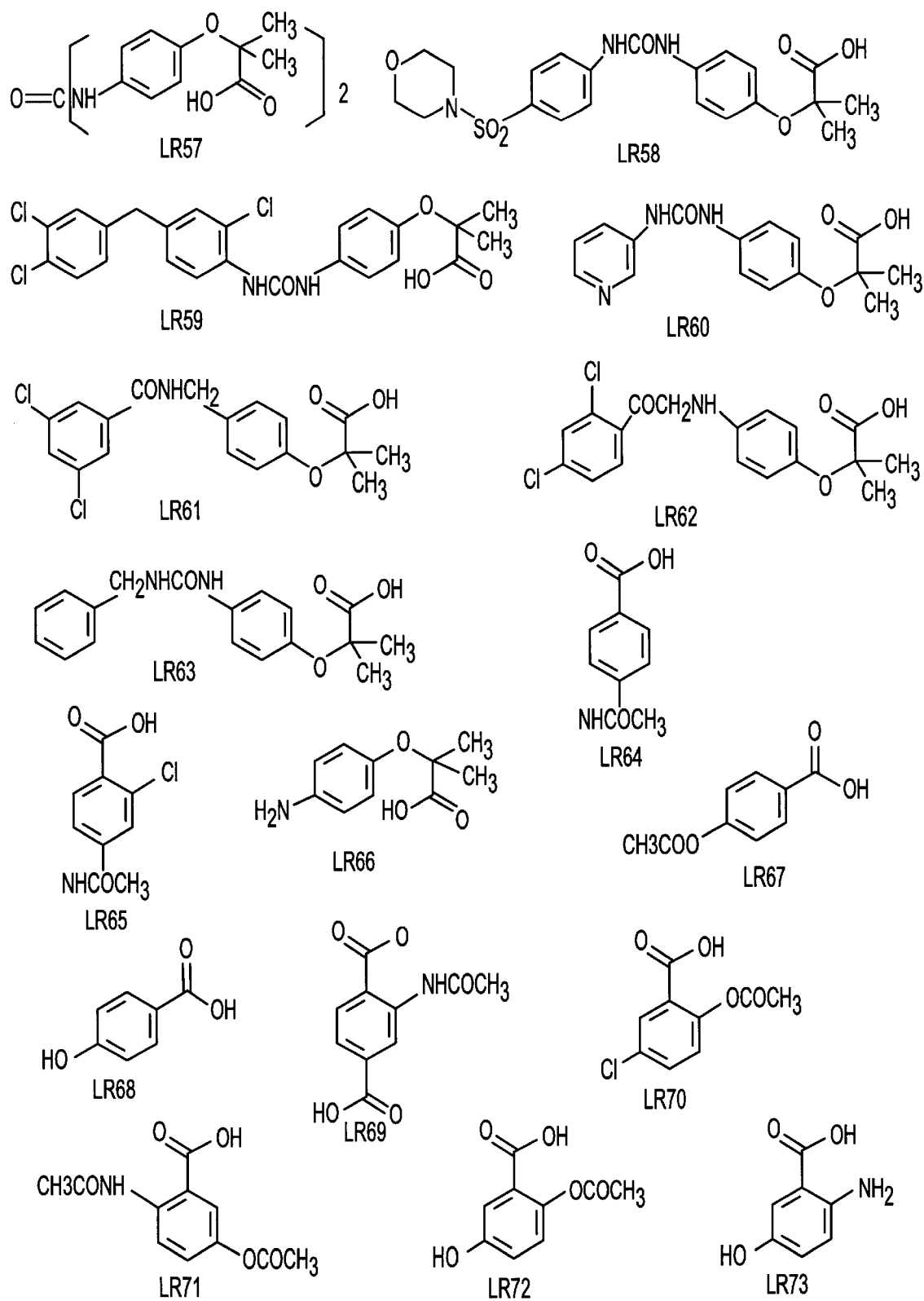
FIG. 9 shows the structures of LR57–LR73.
Figure 10:
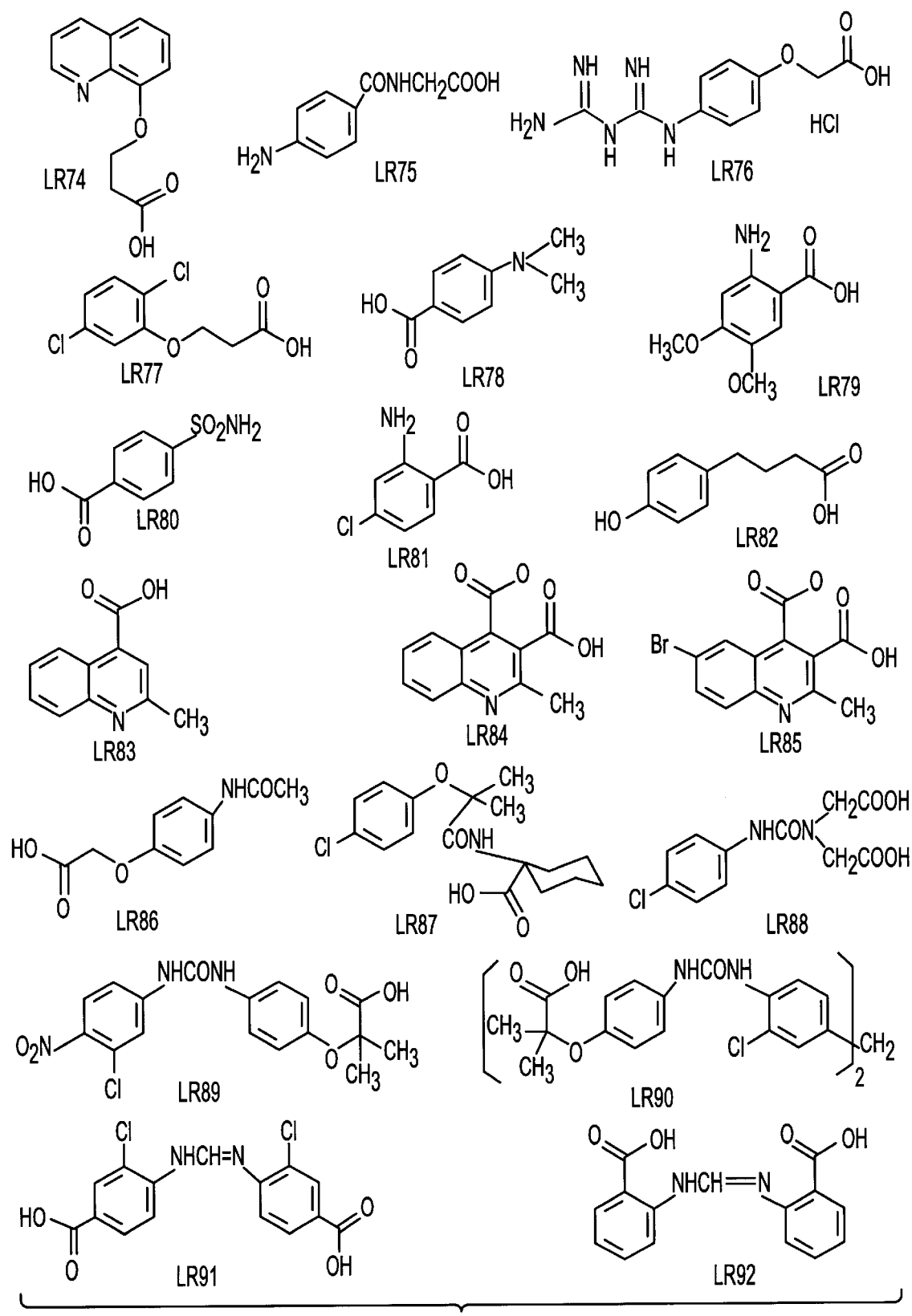
FIG. 10 shows the structures of LR74–LR92.

The compounds of the present invention collectively are defined as derivatives of aryl and heterocyclic ureido and aryl and heterocyclic carboxamido phenoxy isobutyric acids (Rahbar et al., 1999). A general formula encompassing several compounds of the invention is demonstrated in FIG. 1. These compounds are part of a series of compounds originally developed for their effects on the modification of oxygen affinity of hemoglobin by lowering the affinity of hemoglobin for oxygen and shifting the hemoglobin-oxygen-dissociation curve to the right (Rahbar et al., 1987; Lalezari et al., 1988; Lalezari and Lalezari, 1989; U.S. Pat. No. 5,268,500; U.S. Pat. No. 5,292,935; U.S. Pat. No. 5,093,367; U.S. Pat. No. 4,921,997).

Representative compounds of the present invention are shown in FIGS. 5–10 as LR1 to LR92, and were screened for possible inhibitory effects on protein glycation and AGE-formation. For purposes of this disclosure, the names assigned to these structures are: LR1 4-[3-(6-chloro-2,4-(1H, 3H) quinazolinedione)]phenoxyisobutyric acid, MW=374.5

LR2 4-(2-furoylcarboxamido)phenoxyisobutyric acid, MW=289

LR3 (8G5)* 4-(3,5-dichlorophenylureido) phenoxyisobutyric acid, MW=383

LR4 (8p) 4-(4-ethylcarbamatophenylureido) phenoxyisobutyric acid, MW=401

LR5 (8G4) 4-(3,4-dichlorophenylureido) phenoxyisobutyric acid, MW=383

LR6 4-cyclohexylureidophenoxyisobutyric acid, MW=318

LR7 4-(2,3-dichlorophenylureido)phenoxyisobutyric acid, MW=383

LR8 (8nf) 4-(4-carboxaldehydophenylureido) phenoxyisobutyric acid, MW=328

LR9 4-(2-naphthylcarboxamido)phenoxyisobutyric acid, MW=341
LR10 (8c1) 4-(4-methoxyphenylureido)phenoxyisobutyric acid, MW=344
LR11 (8c2) 4-(3,4-dimethoxyphenylureido)phenoxyisobutyric acid, MW=374
LR12 (8k) 4-(4-chloro-3-nitrophenylureido)phenoxyisobutyric acid, MW=393.5
LR13 (8b1) 4-(4-methylphenylureido)phenoxyisobutyric acid, MW=328
LR14 (8c3) 4-(3,4,5-trimetboxyphenylureido)phenoxyisobutyric acid, MW=404
LR15 4-(3-chlorophenylureido)phenoxyisobutyric acid, MW=348.5
LR16 N-4-(nitrophthalimido)phenoxyisobutyric acid, MW=378
LR17 4-(2-thienylcarboxamido)phenoxyisobutyric acid, MW=305
LR18 4-(4-pyridylureido)phenoxyisobutyric acid, MW=300
LR19 4-(3,4,5-trichlorophenylureido)phenoxyisobutyric acid, MW=417.5
LR20 L-bis-[4-(4-chlorobenzamidophenoxyisobutyryl) cystine], MW=871
LR21 4-(3,5-dichlorophenylureido)phenoxyisobutyrylamidomethylcyclohexyl-4-carboxylic acid, MW=522
LR22 DL-N-4-[(3,5-dichlorophenylureido)phenoxyisobutyryl]pipecolic acid, MW=494
LR23 4-(3,5-dichlorophenylureido)phenoxyisobutyryl-1-amidocyclohexane-1-carboxylic acid, MW=508
LR24 4-(4-iodophenylureido)phenoxyisobutyric acid, MW=440
LR25 4-(4-dimethylarninophenylureido)phenoxyisobutyric acid, MW=345
LR26 4-(2,4,6-trichlorophenylureido)phenoxyisobutyric acid, MW=417.5
LR27 4-(2,4,6-trimethylphenylureido)phenoxyisobutyric acid, MW=356
LR28 4-(4-chlorophenoxyacetamido)phenoxyisobutyric acid, MW=363.5
LR29 4-(4-chloro-3-nitrobenzoylcarboxarnido)phenoxyisobutyric acid, MW=406.5
LR30 4-chlorodiphenylurea-4'-carboxylic acid, MW=290.5
LR31 4-(3,4-dichlorophenylacetamido)phenoxyisobutyric acid, MW=382
LR32 diphenylurea-4-carboxylic acid, MW=240
LR33 4-(2-chloro-4-nitrophenylureido)phenoxyisobutyric acid, MW=393.5
LR34 4-(nicotinylamido)phenoxyisobutyric acid, MW=300
LR35 4-chlorophenoxyisobutyric acid, MW=208.5
LR36 4-(benzylsulfonarnido)phenoxyisobutyric acid, MW=349
LR37 4-(2,5-dichlorobenzoylcarboxamido)phenoxyisobutyric acid, MW=396
LR38 L-4-chlorobenzoylphenylalanine, MW=303.5
LR39 2-isopropyl-5-methylphenoxyisobutyric acid, MW=236
LR40 4-(3,4-dimethoxyphenylureido)phenoxyisobutyric acid, MW=374
LR41 4-(3-chloro-4-fluorophenylureido)phenoxyisobutyric acid, MW=393.5
LR42 4-(3,5-dichlorobenzamidoethyl)phenoxyisobutyric acid, MW=384
LR43 4-(phenylureido)phenoxyisobutyric acid, MW=314
LR44 4-(phenylureido-2-chloro)phenoxyisobutyric acid, 348.5
LR45 4-(2,6-dichloro-4-nitrobenzoylcarboxamido)phenoxyisobutyric acid, MW=406.5
LR46 4-(3,5-difluorophenylureido)phenoxyisobutyric acid, MW=350
LR47 4-(N-methyl-4-chlorobenzamido)phenoxyisobutyric acid, MW=347.5
LR48 4-(4-nitrophenylureido)phenoxyisobutyric acid, MW=359
LR49 4-(phenylureido)phenoxyacetic acid, MW=286
LR50 4-(4-chlorobenzoylcarboxarnido)phenoxyisobutyric acid, MW=351.5
LR51 4-(2-hydroxy-4-chlorobenzoylcarboxamido)phenoxyisobutyric acid, MW=377.5
LR52 4-(2-hydroxy-3,5-dichlorobenzoylcarboxamido)phenoxyisobutyric acid, MW=412
LR53 4-(2-chloro-5-nitrophenylureido)phenoxyisobutyric acid, MW=393.5
LR54 4-carboxyphenoxyisobutyric acid, MW=224
LR55 4-(4-carboxyphenylureido)phenoxyisobutyric acid, MW=358
LR56 4-ureidophenoxyisobutyric acid, MW=236
LR57 urea 1,3-bis-4-phenoxyisobutyric acid, MW=416
LR58 4-(4-morpholinosulfonylphenylureido)phenoxyisobutyric acid, MW=463
LR59 4-[(3,4-dichlorophenylmethyl)2-chlorophenylureido]phenoxyisobutyric acid, MW=507.5
LR60 4-(3-pyridylureido)phenoxyisobutyric acid, MW=315
LR61 4-[(3,5-dichlorobenzoylamino)methyl]phenoxyisobutyric acid, MW=382
LR62 4-(2,4-dichlorophenacylamino)phenoxyisobutyric acid, MW=382
LR63 4-(benzylureido)phenoxyisobutyric acid, MW=328
LR64 4-acetamidobenzoic acid
LR65 2-chloro-4-acetamidobenzoic acid
LR66 4-aminophenoxyisobutyric acid
LR67 4-acetoxybenzoic acid
LR68 4-hydroxybenzoic acid
LR69 2-acetamidoterephthalic acid
LR70 5-chloro-2-acetoxybenzoic acid
LR71 2-acetamido-5-acetoxybenzoic acid
LR72 2-acetoxy-5-hydroxybenzoic acid
LR73 2-amino-5-hydroxybenzoic acid
LR74 2-(8-quinolinoxy)propionic acid
LR75 4-aminobenzoylglycine
LR76 N-guanylguanidino-N'-4-phenoxyacetic acid
LR77 2-(2,5-dichlorophenoxy)propionic acid
LR78 4-dimethylaminobenzoic acid
LR79 2-amino-4,5-dimethoxybenzoic acid
LR80 4-sulfonamidobenzoic acid
LR81 2-amino-4-chlorobenzoic acid LR82 4-hydroxyphenylbutyric acid
LR83 2-methyl-4-quinolinecarboxylic acid
LR84 2-methyl-3,4-quinolinedicarboxylic acid
LR85 6-bromo-2-methyl-3,4-quinolinedicarboxylic acid
LR86 4-acetamidophenoxyacetic acid
LR87 1-(4-chlorophenoxybutyrylamido)-1-cyclohexanecarboxylic acid
LR88 4-chlorophenylaminocarbonyliminodiacetic acid
LR89 3-chloro-4-nitrophenylureidophenoxyisobutyric acid
LR90 methylene bis[4,4'-(2-chlorophenylureidophenoxyisobutyric acid)]
LR91 N,N'-bis(2-chloro-4-carboxyphenyl)formamidine
LR92 N,N'-bis(2-carboxyphenyl)formamidine

* The symbols in parentheses are taken from Lalezari and Lalezari (1989).

Although there are 92 compounds in the above list, many of the compounds are quite similar to each other and can be grouped together. For example, compounds LR1 and LR16 are both cyclic ureidophenoxyisobutyric acids; compounds LR2, LR9, LR17, LR20, LR28, LR29, LR31, LR34, LR37, LR38, LR42, LR47, LR50, LR51, LR52, LR61 and LR62 are amidophenoxyisobutyric acids; compounds LR3–LR8, LR10–LR15, LR19, LR21–LR27, LR30, LR32, LR33, LR40, LR41, LR43, LR44, LR46, LR48, LR49, LR53, LR55, LR58–LR60, LR63, LR89 and LR90 are arylureidophenoxyisobutyric acids; compounds LR35, LR39, LR54, LR56, LR57, LR66, LR74, LR76, LR77, LR82, LR86 and LR87 are clofibric acid derivatives; compounds LR91 and LR92 are formimide derivatives; and compounds LR64, LR65, LR67–LR75, LR78 and LR83–LR85 are arylcarboxylic acid derivatives.

The above compounds are capable of inhibiting the formation of advanced glycation end products on target proteins and the resulting protein crosslinking. The rationale of the present invention is to use agents which block the post-glycation step, i.e., the formation of fluorescent chromophores, the presence of which chromophore is associated with and leads to adverse sequelae of diabetes and aging. An ideal agent would prevent the formation of the chromophore and its associated crosslinks of proteins and trapping of proteins on the other proteins, such as occurs in arteries and in the kidneys. The compounds of the invention may be administered to mammals including humans to prevent or reduce protein glycation and crosslinking (protein aging). The compounds may be administered orally at variable dosage depending on the activity of each agent in a single or individual amounts. In addition the compounds may be administered parenterally or rectally. The compounds of the invention, the rationale behind the different assay methods of the present invention, and their use are illustrated by the following Examples.

EXAMPLE 1

Hemoglobin-δ-Gluconolactone (δ-Glu) Assay

Evaluation of early glycation products (Amadori) formation on hemoglobin (HbA$_{1C}$) is performed by incubating red blood cells with an oxidized form of glucose in the presence and the absence of the inhibitor compound followed by determination of (HbA$_{1C}$) in the test versus the control (Rahbar and Nadler., 1999). This test is based on a recent report by Lindsay et al. (1997). δ-Glu, an oxidized analogue of glucose, can react rapidly with hemoglobin within the red cells and significantly increases the HbA$_{1C}$ levels within hours after incubation. By contrast, glucose requires weeks for an equivalent reaction to occur. We have used this finding to devise an assay method to measure early stage glycation of hemoglobin (Amadori product) and an assay to evaluate the ability of an inhibitor to inhibit HbA$_{1C}$ formation. Briefly, fresh blood was drawn in potassium-EDTA and prepared for incubation within 30 minutes of collection by mixing 200 μL of blood with 40 μL of either phosphate buffered-saline (PBS), pH 7.4, alone, PBS containing 50 millimoles/L δ-Glu (Sigma), or PBS containing 50 millimoles/L δ-Glu plus 1 millimole/L inhibitor. After incubation for 5 hours at 37° C., the percentage of glycated hemoglobin present was determined. The percentage of glycated Hb (HbA$_{1C}$) was determined using a dedicated ion-exchange HPLC system (BIORAD DIAMAT). Blood samples were analyzed in triplicate. The % inhibition of HbA$_{1C}$ formation by the compound was calculated according to the following formula:

$$((B-C)/(B-A)) \times 100$$

where A is HbA$_{1C}$ concentration in the baseline control tube not treated with δ-Glu, B is the HbA$_{1C}$ concentration in blood incubated with δ-Glu, C is the HbA$_{1C}$ content of the test tube treated both with δ-Glu and the inhibitor compound.

The amount of (HbA$_{1C}$) formation using δ-Glu treated whole blood from normal volunteers using 1 millimole/L of the compounds is shown in FIGS. 2A–B for selected compounds. The results, calculated as percent inhibition of HbA$_{1c}$ formation, for all 92 LR compounds are shown in Table 1. FIGS. 2A–B show results from a single assay whereas the results shown in Table 1 are an average of 3 determinations.

The above experiment suggests that this type of drug therapy has benefits in reducing the pathology associated with the formation of early glycation products, a preliminary step in the advanced glycation end product formation.

EXAMPLE 2

BSA-Glucose Assay

This test is used to evaluate the ability of the inhibitors to inhibit glucose-mediated development of fluorescence of BSA (Ikeda et al., 1996). BSA (fraction V) from Sigma 50 mg/mL and 800 mM glucose (144 mg/mL) in 1.5 M phosphate buffer pH 7.4 containing NaN$_3$ 0.2 g/L was incubated under aseptic conditions at 37° C. for 7 days in the presence or absence of various concentrations of the compounds. After 7 days of incubation each sample was examined for the development of specific fluorescence (excitation, 370 nm; emission, 440 nm). The % inhibition of AGE formation in the test sample versus control was calculated for each inhibitor compound. Aminoguanidine (50 mM) was used as a positive control.

FIGS. 3A–B show for a selection of the tested compounds the inhibitory effects of 1 millimole/L of the new inhibitor versus 50 millimoles/L of aminoguanidine. The data presented in FIGS. 3A–B are from 1 determination. Results which are averaged for 3 determinations for each of the 92 compounds are tabulated in Table 1.

TABLE 1

| Compound | δ-Glu Assay | G.K.-Ribose Assay | BSA-Glucose Assay |
|---|---|---|---|
| AG | 12.1 | 67.0 | 74.0 |
| LR1 | 28.8 | 11.2 | 24.8 |
| LR2 | 17.3 | 36.8 | 45.0 |
| LR3 | 25.0 | 40.0 | 46.2 |
| LR4 | 19.2 | 42.5 | 48.7 |
| LR5 | 36.5 | 33.6 | 66.2 |
| LR6 | 25.0 | 9.1 | 57.5 |
| LR7 | 19.2 | 27.5 | 39.6 |
| LR8 | 21.0 | 23.6 | 47.5 |
| LR9 | 17.7 | 0.0 | 31.2 |
| LR10 | 22.5 | 20.5 | 56.2 |
| LR11 | 25.8 | 18.6 | 50.0 |
| LR12 | 22.5 | 43.6 | 55.0 |
| LR13 | 21.0 | 27.5 | 48.1 |
| LR14 | 22.5 | 18.6 | 49.3 |
| LR15 | 22.5 | 30.0 | 58.1 |
| LR16 | 35.1 | 0.0 | 29.1 |
| LR17 | 46.4 | 26.4 | 12.5 |
| LR18 | 58.1 | 26.2 | 37.5 |
| LR19 | 41.0 | 40.0 | 28.4 |
| LR20 | 52.8 | 31.0 | 12.8 |
| LR21 | 50.1 | 15.0 | 7.1 |
| LR22 | 42.7 | 10.0 | 14.2 |
| LR23 | 45.0 | 70.0 | 42.6 |
| LR24 | 50.0 | 41.4 | 31.2 |
| LR25 | 52.0 | 30.5 | 41.5 |
| LR26 | 73.8 | 47.1 | 38.9 |
| LR27 | 50.0 | 52.5 | 52.0 |
| LR28 | 50.0 | 63.3 | 78.8 |
| LR29 | 52.0 | 53.1 | 44.2 |
| LR30 | 63.6 | 18.1 | 16.2 |
| LR31 | 54.5 | 9.6 | 13.3 |
| LR32 | 47.7 | 9.5 | 32.7 |
| LR33 | 70.4 | 25.1 | 41.1 |
| LR34 | 52.2 | 15.1 | 24.0 |
| LR35 | 47.7 | 5.7 | 42.4 |
| LR36 | 56.8 | 30.1 | 44.4 |
| LR37 | 40.9 | 41.2 | 47.7 |
| LR38 | 50.9 | 20.2 | 13.8 |
| LR39 | 56.8 | 18.6 | 21.2 |
| LR40 | 50.9 | 30.6 | 32.0 |
| LR41 | 60.7 | 35.4 | 37.4 |
| LR42 | 47.0 | 21.8 | 46.8 |
| LR43 | 58.8 | 21.5 | 44.0 |
| LR44 | 58.8 | 13.0 | 42.1 |
| LR45 | 56.8 | 31.7 | 49.5 |
| LR46 | 55.7 | 21.1 | 30.1 |
| LR47 | 54.0 | 30.5 | 34.7 |
| LR48 | 45.9 | 31.0 | 45.5 |
| LR49 | 57.3 | 22.9 | 41.3 |
| LR50 | 57.3 | 27.3 | 42.7 |
| LR51 | 52.0 | 0* | 0* |
| LR52 | 58.3 | 0* | 0* |
| LR53 | 54.1 | 13.6 | 20.4 |
| LR54 | 54.1 | 4.9 | 22.8 |
| LR55 | 56.2 | 11.0 | 36.8 |
| LR56 | 46.2 | 2.1* | 39.1* |
| LR57 | 48.1 | 0* | 31.1* |
| LR58 | 40.7 | 4.5* | 49.0* |
| LR59 | 48.1 | 8.0 | 39.4 |
| LR60 | 29.6 | 0* | 47.8* |
| LR61 | 46.2 | 13.1 | 62.0 |
| LR62 | 53.7 | 26.0 | 49.1 |
| LR63 | 40.7 | 10.9 | 60.2 |
| LR64 | 49 | 24.7 | 16.9 |
| LR65 | 47 | 39.2 | 26.3 |
| LR66 | 49 | 41.3 | 28.9 |
| LR67 | 47 | 31.1 | 30.7 |
| LR68 | 41.1 | 30.5 | 24.3 |
| LR69 | 35.2 | 32.3 | 44 |
| LR70 | 49 | 36.7 | 49.2 |
| LR71 | 39.2 | 41.1 | 76.1 |
| LR72 | 77.2 | 22.9 | 27.3 |
| LR73 | 43.1 | 18.3 | 18.9 |
| LR74 | 22.9 | 38.6 | 11.8 |
| LR75 | 21.3 | 12.9 | 21.9 |
| LR76 | 13.1 | 39.8 | 27.9 |
| LR77 | 52.7 | 19.2 | 24.7 |
| LR78 | 52.7 | 32.6 | 20.9 |
| LR79 | 54.5 | 48.1 | 43.1 |
| LR80 | 20 | 52.1 | 56.6 |
| LR81 | 52.7 | 10.9 | 27.4 |
| LR82 | 52.7 | 34 | 10.3 |
| LR83 | 43.6 | 24.8 | 29 |
| LR84 | 49 | 18.1 | 28.1 |
| LR85 | 47.2 | 12.9 | 44.5 |
| LR86 | 49 | 30.3 | 63 |
| LR87 | 54.5 | 10.9 | 22.4 |
| LR88 | 52.7 | 9.4 | 20.8 |
| LR89 | 44.9 | 43 | 35.4 |
| LR90 | 38.7 | 30.5 | 14.5 |
| LR91 | 34.7 | 34.2 | 49.5 |
| LR92 | 42.8 | 82.6 | 89.3 |

*These compounds have an intrinsic fluorescence which interferes with the assay.

EXAMPLE 3

N-Acetyl-Glycyl-Lysine Methyl Ester (G.K. Peptide)—Ribose Assay

Evaluation of the late glycation products (AGE's), and AGE-inhibition by the new inhibitor compounds was tested by incubation of G.K. peptide in ribose in the presence or the absence of the agent, followed by determination of chromophores generated in the course of glycation and AGE formation through determination of their specific fluorescence. The Nagaraj et al. (1996) method used to evaluate the ability of the compounds of the present invention to inhibit the crosslinking of N-acetylglycyl-lysine methyl ester in the presence of ribose was as follows:

Stock Solutions:

0.5 M sodium phosphate buffer pH 7.4 containing $NaN_3$ 0.2 g/L

GK peptide (Sigma) 80 mg/mL in 0.5 M sodium phosphate buffer pH 7.4

Ribose 800 mM (120 mg/mL) in 0.5 M phosphate buffer

Equal volumes (0.1 mL) of the 3 stock solutions were mixed together, filtered through a 0.2 micron filter (Coming) and incubated under aseptic conditions for 24 hours at 37° C. The inhibitor compounds were added to a final concentration of 1 millimole/L. At the end of the incubation period, samples were analyzed for their specific fluorescence (excitation, 340 nm; emission, 420 nm). The % inhibition by different concentrations of inhibitor was calculated as described above. Aminoguanidine was used at 50 mM as a positive control.

FIGS. 4A–B show the inhibitory effects of a selection of the compounds to block specific fluorescence of protein-AGE in these separate determinations, using G.K. peptide-ribose assay. Results for all 92 compounds are shown in Table 1. FIGS. 4A–B show the results of a single assay whereas the data in Table 1 are the averaged results for 3 assays of each compound. The results obtained from the above two experiments (Examples 2 and 3) suggest this type of drug therapy has benefits in reducing the pathology associated with the formation of late glycation products and protein crosslinking.

EXAMPLE 4

Lysozyme-Glucose or Fructose Crosslinking Assay

Lysozyme-glucose or fructose crosslinking assays according to Taneda and Monnier (1994) are in vitro assays which were performed to evaluate the inhibitory effect of compounds on AGE-derived crosslinking and AGE-protein formation. Egg white lysozyme (Sigma) and glucose or fructose in 0.2 M sodium phosphate pH 7.4 containing 0.2 g/L NaN$_3$ were mixed with various test compounds to give a final concentration of 1 millimole/L of test compound, 100 mg/mL egg white lysozyme, and 200 mM glucose or 100 mM fructose. All samples were incubated under aseptic conditions at 37° C. for 7 days. After 7 days, each sample was analyzed for the determination of AGE-derived crosslinking and AGE-formation. Aliquots were applied to 20% SDS-PAGE gels under reducing conditions and stained with Coomassie blue.

EXAMPLE 5

ELISA Assay

A special ELISA technique (Al-abed et al., 1999) was used to evaluate the ability of the compounds being studied to inhibit the crosslinking of glycated-BSA (AGE-BSA) to a rat tail-tendon-collagen coated 96 well plate (Biocoat microtiter plates from Collaborative Research. Crosslinking of AGE-BSA to a rat tail-tendon-collagen coated plate was performed with and without the testing compound at the desired concentrations. The uncross-linked AGE-BSA was then removed by washing the wells. The AGE-BSA crosslinked to the tail-tendon-collagen coated plate was then quantified by a polyclonal antibody raised against AGE-RNase. Positive results in the assay indicate that the inhibitor is capable of reducing the amount of AGE-BSA which crosslinks with collagen. Aminoguanidine was used as positive control.

Figure 11A:
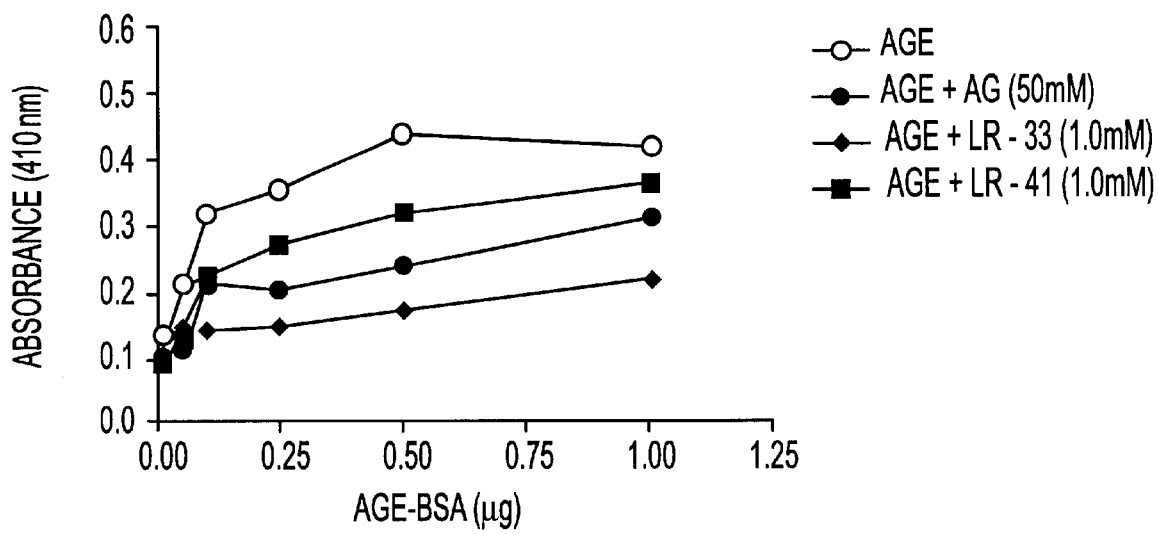
FIGS. 11A–B show the results of immunochemical studies on the inhibitory effects of representative compounds using a specific ELISA assay in which inhibition of crosslinking of collagen with AGE-BSA is measured.
Figure 11B:
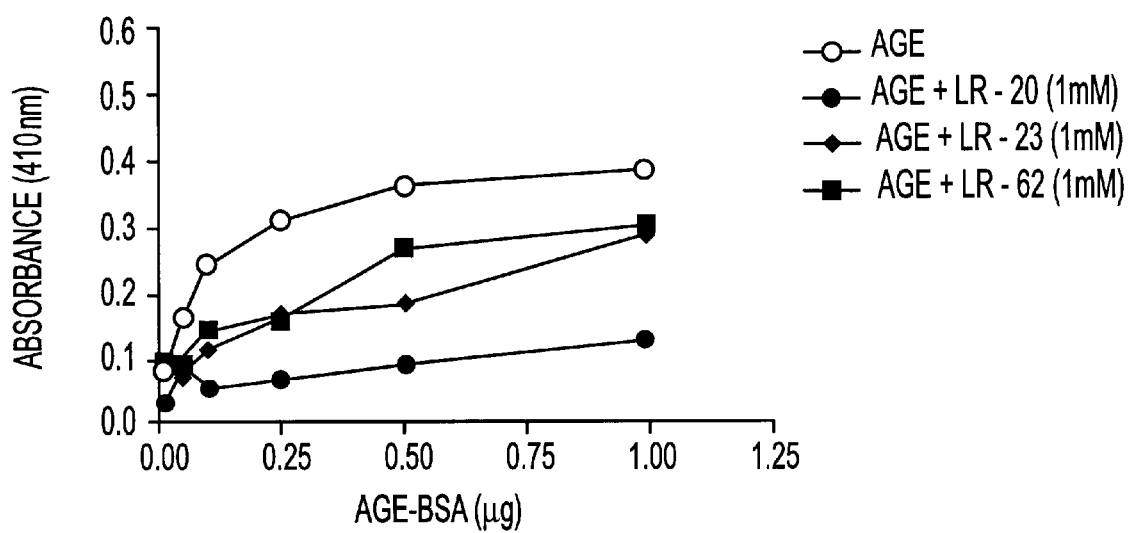

The results using five representative compounds are shown in FIGS. 11A–B. The five compounds (LR33, LR41, LR20, LR23 and LR62) are among a number of strong inhibitors of AGE-protein crosslinking. Percent inhibitions of the control were calculated to be 61% for LR33 and 27.4% for LR41 at 1 mmole/L and 45.5% for aminoguanidine at 50 mM.

EXAMPLE 6

Ribonuclease-Ribose Fluorescence—Inhibition and Crosslinking-Inhibition Assays Bovine pancreatic ribonuclease A (RNase A) has been extensively used as a model protein to study protein glycation and AGE formation, as well as the kinetics of AGE-formation (Khalifah et al., 1996). RNase A has the advantage of not precipitating during glycation reaction whereas lysozyme tends to precipitate during glycation with ribose and glucose.

The RNase-ribose assay measures the fluorescence generated as a result of AGE-formation in the presence or absence of the inhibitor as compared to aminoguanidine. This assay is also used to detect the inhibitory effects of a compound on protein-crosslinking and the formation of dimers and trimers as shown by SDS-PAGE.

Both uninterrupted and interrupted versions of this assay (Nagaraj et al., 1996) have been performed successfully. However, the interrupted technique worked better in our hands. Bovine RNase A type I-A (Sigma) was used throughout our assays.

For the uninterrupted method, RNase, 1 mg/mL, was incubated with ribose (0.2 M) at 37° C. in 0.4 M sodium phosphate buffer pH 7.5 containing 0.02% sodium azide for 7 days in the dark. Prospective inhibitor was added to the reaction at the beginning of the incubation period. All solutions were prepared in sterile condition by filtering through a 0.2 micron filter (Corning). At the end of the incubation, samples were analyzed for their fluorescence (excitation, 330 nm; emission, 400 nm). The percent of inhibition of AGE-formation by different concentrations of the inhibitor were calculated as described before.

Interrupted RNase-ribose assays were carried out as follows: RNase, 10 mg/mL, was incubated with ribose (0.5 M) at 37° C. in 0.4 M sodium phosphate buffer pH 7.5 containing 0.02% sodium azide for 24 hours in the absence of inhibitor compound. Glycation was then interrupted by diluting the reaction 1:100 in 0.4 M phosphate buffer and adding the inhibitor under study to the reaction at the desired concentrations. The reaction was filtered through a 0.2 micron filter and incubated at 37° C. in the dark for four additional days. At the end of the incubation period, samples were analyzed for their fluorescence as described before, and the percent inhibition was calculated.

For detection of the inhibitory effects of the compound under the study, the inhibitory effect being the inhibition of RNase crosslinking and dimer-trimer formation, at the end of the incubation period the samples were analyzed by SDS-PAGE technique as described before. In the case of the interrupted glycation assays, the samples were concentrated by using Centricon 10 (Amicon) and then applied to the gels.

The above Examples suggest that this type of drug therapy will be beneficial in reducing the pathology associated with the formation of nonenzymatic glycation products (early and late products) and protein-protein crosslinking. Compounds of the present invention are found to be 10 to 40 times more potent inhibitors of AGE-formation in vitro as compared to aminoguanidine which is in phase 2/3 clinical trial to prevent diabetic complications. Previous studies have shown these compounds to be non-toxic. They may be administered orally at variable dosages depending on the activity of each agent in a single or individual amounts. In addition, the compounds may be administered parenterally or rectally.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Airaksinen K E J, et al. (1993). *Cardiovas. Res.* 27:942–945.
Al-Abed, et al. (1999). *Methods in Enzymology* 309:152–172.
Boel E, et al. (1995). *J. Diab. Compl.* 9:104–129.
Booth A A, et al. (1997). *J. Biol. Chem.* 272:5430–5437.
Brownlee M, et al. (1985). *Diabetes* 34:938–941.
Brownlee M, et al. (1986). *Science* 232:1629–1632.
Brownlee M, et al. (1991). *N. Engl. J. Med.* 318:1315–1321.
Bucala R and Cerami A (1992). *Adv. Pharmacol.* 23:1–33.
Bucala R and Viassara H (1997). *Experimental Physiology* 82:327–337.
Bucala R, et al. (1984). *Proc. Natl. Acad. Sci. USA* 81:105–109.
Bucala R, et al. (1993). *Proc. Natl. Acad. Sci. USA* 90:6434–6438.
Bucala R, et al. (1994). *Proc. Natl. Acad Sci. USA* 91:9441–9445.
Cameron N E, et al. (1992). *Diabetologia* 35:946–950.

Corbett J A, et al. (1992). *Diabetes* 41:552–556.
Dawnay A and Millar D J (1998). *Cell. Mol. Biol.* (Noisy-le-grand) 44:1081–1094.
Durany N, et al. (1999). *Eur. Arch. Psychiatry Clin. Neurosci.* 249 Suppl. 3:68–73.
Edelstein D and Brownlee M (1992). *Diabetes* 41:26–29.
Haitoglou C S, et al. (1992). *J. Biol. Chem.* 267:12404–12407.
Hammes H, et al. (1991). *Proc. Natl. Acad. Sci. USA* 88:11555–11563.
Harding J J (1990). *Arch. Opthalmol.* 108:13–14.
Hirsch J, et al. (1992). *Carbohydrate Res.* 232:125–130.
Horie K, et al. (1997). *J. Clin. Invest.* 100:2995–3004.
Ikeda K, et al. (1996). *Biochemistry* 35:8075–8083.
Itakura M, et al. (1991). *Life Science* 49:889–897.
Kato H, et al. (1 990). *Biochim. Biophys. Acta* 1035:71–76.
Kato S, et al. (1999). *Acta Neuropathol.* (Berl.) 97:260–266.
Kennedy L and Lyons T J (1997). *Metabolism* 46:14–21.
Khalifah R G, et al. (1996). *Biochemistry* 35:4645–4654.
Kikuchi S, et al. (1999). *J. Neurosci. Res.* 57:280–289.
Kochakian M, et al. (1996). *Diabetes* 45:1694–1700.
Koschinsky T, et al. (1997). *Proc. Natl. Acad. Sci. USA* 94:6474–6479.
Lalezari I, et al. (1988). *Proc. Natl. Acad. Sci. USA* 85:6117–6121.
Lalezari I and Lalezari P (1989). *J. Med. Chem.* 32:2352–2357.
Li Y M, et al. (1996). *Proc. Natl. Acad. Sci. U.S.A.* 93:3902–3907.
Lindsay M R, et al. (1997). *Clin. Chem. Acta* 263:239–247.
Lucey M D, et al. (2000). *J. Rheumatol.* 27:319–323.
Maillard L C (1916). *Ann. Chem.* 5:258.
Makita Z, et al. (1991). *N. Eng. J. Med.* 325:836–842.
Makita Z, et al. (1992). *Science* 258:651–653.
Makita Z, et al. (1994). *Lancet* 343:1519–1522.
Matsumoto K, et al. (1997). *Biochem. Biophys. Res. Commun.* 24:352–354.
McPherson J D, et al. (1988). *Biochemistry* 27:1901–1907.
Miyata T, et al. (1993). *J. Clin. Invest.* 92:1243–1252.
Monnier V, et al. (1986). *N. Engl. J. Med.* 314:403–408.
Munch G, et al. (1997). *Brain Res. Brain Res. Rev.* 23:134–143.
Munch G, et al. (1998). *J. Neural. Transm.* 105:439–461.
Nagaraj R H, et al. (1996). *J. Biol. Chem.* 271:19338–19345.
Nakamura S, et al. (1997). *Diabetes* 46:895–899.
Newkirk M M, et al. (1998). *Cell. Mol. Biol.* (Noisy-le-grand) 44:1129–1138.
Nicholl I D and Bucala R (1998). *Cell. Mol Biol.* (Noisy-le-grand) 44:1025–1033.
Nicholls K and Mandel T (1989). *Lab. Invest.* 60:486–491.
Odani H, et al. (1999). *J. Chromatogr. B Biomed Sci. Appl.* 731:131–140.
Panagiotopoulos S, et al. (1998). *Atherosclerosis* 136:125–131.
Rahbar S (1968). *Clin. Chem. Acta* 22:296–298.
Rahbar S, et al. (1969). *Biochem. Biophys. Res. Commun.* 36:838–843.
Rahbar S, et al. (1987). *Blood* 70 (Suppl. 1):171.
Rahbar S, et al. (1999). *Biochem. Biophys. Res. Commun.* 262:651–656.
Rahbar S and Nadler J L (1999). *Clin. Chim. Acta* 287:123–130.
Requena J R, et al. (1993). *Diabetes Res. Clin. Pract.* 19:23–30.
Sano H, et al. (1999). *Mech. Ageing Dev.* 107:333–346.
Sensi M, et al. (1993). *Diabetologia* 36:797–801.
Shibata N, et al. (1999). *Acta Neuropathol.* (Berl) 97:240–246.
Silbiger S, et al., (1993). *Kidney Int.* 43:853–864.
Soulis T, et al. (1997). *Diabetologia* 40:1141–1151.
Soulis-Liparota T, et al. (1991). *Diabetes* 40:1328–1334.
Takagi Y, et al. (1995). *J. Diabetes Compl.* 9:87–91.
Takayarna F, et al. (1998). *Cell. Mol. Biol.* (Noisy-le-grand) 44:1101–1109.
Taneda S and Monnier V M (1994). *Clin. Chem.* 40:1766–1773.
Tilton R G, et al. (1993). *Diabetes* 42:221–232.
Ulrich P and Zhang X (1997). *Diabetologia* 40:5157–5159.
Vasan S, et al. (1996). *Nature* 382:275–278.
Vlassara H (1994). *J. Lab. Clin. Med.* 124:19–30.
Vlassara H, et al. (1994). *Lab. Invest.* 70:138–151.
Vlassara H, et al. (1995). *Mol. Med.* 1:447–456.

PATENTS

U.S. Pat. No. 4,921,997
U.S. Pat. No. 5,093,367
U.S. Pat. No. 5,268,500
U.S. Pat. No. 5,292,935

What is claimed is:

1. A method of inhibiting formation of glycation endproducts or protein crosslinking resulting from glycation in a mammal in which it is desired to inhibit formation of glycation endproducts or protein crosslinking, wherein said method comprises administering an amount of a compound or a pharmaceutically acceptable salt of said compound to said mammal wherein said amount is effective in inhibiting formation of glycation endproducts or protein crosslinking, wherein said compound is selected from the group consisting of:

4-[3-(6-chloro-2,4-(1H, 3H) quinazolinedione)] phenoxyisobutyric acid;

4-(2-furoylcarboxamido)phenoxyisobutyric acid;

4-(3,5-dichlorophenylureido)phenoxyisobutyric acid;

4-(4-ethylcarbamatophenylureido)phenoxyisobutyric acid;

4-(3,4-dichlorophenylureido)phenoxyisobutyric acid;

4-cyclohexylureidophenoxyisobutyric acid;

4-(2,3-dichlorophenylureido)phenoxyisobutyric acid;

4-(4-carboxaldehydophenylureido)phenoxyisobutyric acid;

4-(2-naphthylcarboxamido)phenoxyisobutyric acid;

4-(4-methoxyphenylureido)phenoxyisobutyric acid;

4-(3,4-dimethoxyphenylureido)phenoxyisobutyric acid;

4-(4-chloro-3-nitrophenylureido)phenoxyisobutyric acid;

4-(4-methylphenylureido)phenoxyisobutyric acid;

4-(3,4,5-trimethoxyphenylureido)phenoxyisobutyric acid;

4-(3-chlorophenylureido)phenoxyisobutyric acid;

N-4-(nitrophthalimido)phenoxyisobutyric acid;

4-(2-thienylcarboxamido)phenoxyisobutyric acid;

4-(4-pyridylureido)phenoxyisobutyric acid;

4-(3,4,5-trichlorophenylureido)phenoxyisobutyric acid;

L-bis-[4-(4-chlorobenzamidophenoxyisobutyryl)cystine];

4-(3,4-dichlorophenylureido) phenoxyisobutyrylamidomethylcyclohexyl-4-carboxylic acid;

DL-N-4-[(3,4-dichlorophenylureido)phenoxyisobutyryl] pipecolic acid;

4-(3,5-dichlorophenylureido)phenoxyisobutyryl-1-amidocyclohexane-1-carboxylic acid;

4-(4-iodophenylureido)phenoxyisobutyric acid;
4-(4-dimethylaminophenylureido)phenoxyisobutyric acid;
4-(2,4,6-trichlorophenylureido)phenoxyisobutyric acid;
4-(2,4,6-trimethylphenylureido)phenoxyisobutyric acid;
4-(4-chlorophenoxyacetamido)phenoxyisobutyric acid;
4-(4-chloro-3-nitrobenzoylcarboxamido)phenoxyisobutyric acid;
4-chlorodiphenylurea-4'-carboxylic acid;
4-(3,4-dichlorophenylacetamido)phenoxyisobutyric acid;
diphenylurea-4-carboxylic acid;
4-(2-chloro-4-nitrophenylureido)phenoxyisobutyric acid;
4-(nicotinylamido)phenoxyisobutyric acid;
4-chlorophenoxyisobutyric acid;
4-(benzylsulfonamido)phenoxyisobutyric acid;
4-(2,5-dichlorobenzoylcarboxamido)phenoxyisobutyric acid;
L-4-chlorobenzoylphenylalanine;
2-isopropyl-5-methylphenoxyisobutyric acid;
4-(3,4-dimethoxyphenylureido)phenoxyisobutyric acid;
4-(3-chloro-4-fluorophenylureido)phenoxyisobutyric acid;
4-(3,5-dichlorobenzamidoethyl)phenoxyisobutyric acid;
4-(phenylureido)phenoxyisobutyric acid;
4-(phenylureido-2-chloro)phenoxyisobutyric acid;
4-(2,6-dichloro-4-nitrobenzoylcarboxarnido)phenoxyisobutyric acid;
4-(3,5-difluorophenylureido)phenoxyisobutyric acid;
4-(N-methyl-4-chlorobenzamido)phenoxyisobutyric acid;
4-(4-nitrophenylureido)phenoxyisobutyric acid;
4-(phenylureido)phenoxyacetic acid;
4-(4-chlorobenzoylcarboxamido)phenoxyisobutyric acid;
4-(2-hydroxy-4-chlorobenzoylcarboxamido)phenoxyisobutyric acid;
4-(2-hydroxy-3,5-dichlorobenzoylcarboxamido)phenoxyisobutyric acid;
4-(2-chloro-5-nitrophenylureido)phenoxyisobutyric acid;
4-carboxyphenoxyisobutyric acid;
4-(4-carboxyphenylureido)phenoxyisobutyric acid;
2-ureidophenoxyisobutyric acid;
urea 1,3-bis-4-phenoxyisobutyric acid;
4-(4-morpholinosulfonylphenylureido)phenoxyisobutyric acid;
4-[(3,4-dichlorophenylmethyl)2-chlorophenylureido]phenoxyisobutyric acid;
4-(3-pyridylureido)phenoxyisobutyric acid;
4-[(3,5-dichlorobenzoylamino)methyl]phenoxyisobutyric acid;
4-(2,4-dichlorophenacylamino)phenoxyisobutyric acid;
4-(benzylureido)phenoxyisobutyric acid;
4-acetamidobenzoic acid;
2-chloro-4-acetamidobenzoic acid;
4-aminophenoxyisobutyric acid;
2-acetamidoterephthalic acid;
5-chloro-2-acetoxybenzoic acid;
2-acetamido-5-acetoxybenzoic acid;
2-amino-5-hydroxybenzoic acid;
2-(8-quinolinoxy)propionic acid;
N-guanylguanidino-N'-4-phenoxyacetic acid;
2-(2,5-dichlorophenoxy)propionic acid;
4-dimethylaminobenzoic acid;
2-amino4,5-dimethoxybenzoic acid;
4-sulfonamidobenzoic acid;
2-amino-4-chlorobenzoic acid;
4-hydroxyphenylbutyric acid;
2-methyl-4-quinolinecarboxylic acid;
2-methyl-3,4-quinolinedicarboxylic acid;
6-bromo-2-methyl-3,4-quinolinedicarboxylic acid;
4-acetamidophenoxyacetic acid;
1-(4-chlorophenoxybutyrylamido)-1-cyclohexanecarboxylic acid;
4-chlorophenylaminocarbonyliminodiacetic acid;
3-chloro-4-nitrophenylureidophenoxyisobutyric acid;
methylene bis [4,4'-(2-chlorophenylureidophenoxyisobutyric acid)];
N,N'-bis(2-chloro-4-carboxyphenyl)formamidine; and
N,N'-bis(2-carboxyphenyl)formamidine.

2. The method of claim 1 wherein said compound is selected from the group consisting of:
L-bis-[4-(4-chlorobenzamidophenoxyisobutyryl)cystine];
4-(3,5-dichlorophenylureido)phenoxyisobutyryl-1-amidocyclohexane-1-carboxylic acid;
4-(2-chloro-4-nitrophenylureido)phenoxyisobutyric acid;
4-(3-chloro-4-fluorophenylureido)phenoxyisobutyric acid;
4-(2,4-dichlorophenacylamino)phenoxyisobutyric acid; and
methylene bis [4,4'-(2-chlorophenylureidophenoxyisobutyric acid)].

3. The method of claim 1 wherein said compound is selected from the group consisting of:
4-(2,4,6-trichlorophenylureido)phenoxyisobutyric acid;
4-[(3,4-dichlorophenylmethyl)2-chlorophenylureido]phenoxyisobutyric acid; and
N,N'-bis(2-chloro-4-carboxyphenyl)formamidine.

4. A method of slowing deleterious effects of aging in a mammal in which it is desired to slow the deleterious effects of aging wherein said effects are formation of glycation endproducts or protein crosslinking resulting from glycation, wherein said method comprises administering an amount of a compound or a pharmaceutically acceptable salt of said compound to said mammal wherein said amount is effective to inhibit formation of glycation endproducts or protein crosslinking, wherein said compound is selected from the group consisting of:
4-[3-(6-chloro-2,4-(1H, 3H) quinazolinedione)]phenoxyisobutyric acid;
4-(2-fiuroylcarboxamido)phenoxyisobutyric acid;
4-(3,5-dichlorophenylureido)phenoxyisobutyric acid;
4-(4-ethylcarbamatophenylureido)phenoxyisobutyric acid;
4-(3,4-dichlorophenylureido)phenoxyisobutyric acid;
4-cyclohexylureidophenoxyisobutyric acid;
4-(2,3-dichlorophenylureido)phenoxyisobutyric acid;
4-(4-carboxaldehydophenylureido)phenoxyisobutyric acid;
4-(2-naphthylcarboxamido)phenoxyisobutyric acid;

4-(4-methoxyphenylureido)phenoxyisobutyric acid;
4-(3,4-dimethoxyphenylureido)phenoxyisobutyric acid;
4-(4-chloro-3-nitrophenylureido)phenoxyisobutyric acid;
4-(4-methylphenylureido)phenoxyisobutyric acid;
4-(3,4,5-trimethoxyphenylureido)phenoxyisobutyric acid;
4-(3-chlorophenylureido)phenoxyisobutyric acid;
N-4-(nitrophthalimido)phenoxyisobutyric acid;
4-(2-thienylcarboxamido)phenoxyisobutyric acid;
4-(4-pyridylureido)phenoxyisobutyric acid;
4-(3,4,5-trichlorophenylureido)phenoxyisobutyric acid;
L-bis-[4-(4-chlorobenzamidophenoxyisobutyryl)cystine];
4-(3,4-dichlorophenylureido)phenoxyisobutyrylamidomethylcyclohexyl-4-carboxylic acid;
DL-N-4-[(3,4-dichlorophenylureido)phenoxyisobutyryl] pipecolic acid;
4-(3,5-dichlorophenylureido)phenoxyisobutyryl-1-amidocyclohexane-1-carboxylic acid;
4-(4-iodophenylureido)phenoxyisobutyric acid;
4-(4-dimethylaminophenylureido)phenoxyisobutyric acid;
4-(2,4,6-trichlorophenylureido)phenoxyisobutyric acid;
4-(2,4,6-trimethylphenylureido)phenoxyisobutyric acid;
4-(4-chlorophenoxyacetamido)phenoxyisobutyric acid;
4-(4-chloro-3-nitrobenzoylcarboxarnido)phenoxyisobutyric acid;
4-chlorodiphenylurea-4'-carboxylic acid;
4-(3,4-dichlorophenylacetamido)phenoxyisobutyric acid;
diphenylurea-4-carboxylic acid;
4-(2-chloro-4-nitrophenylureido)phenoxyisobutyric acid;
4-(nicotinylamido)phenoxyisobutyric acid;
4-chlorophenoxyisobutyric acid;
4-(benzylsulfonamido)phenoxyisobutyric acid;
4-(2,5-dichlorobenzoylcarboxarnido)phenoxyisobutyric acid;
L-4-chlorobenzoylphenylalanine;
2-isopropyl-5-methylphenoxyisobutyric acid;
4-(3,4-dimethoxyphenylureido)phenoxyisobutyric acid;
4-(3-chloro-4-fluorophenylureido)phenoxyisobutyric acid;
4-(3,5-dichlorobenzamidoethyl)phenoxyisobutyric acid;
4-(phenylureido)phenoxyisobutyric acid;
4-(phenylureido-2-chloro)phenoxyisobutyric acid;
4-(2,6-dichloro-4-nitrobenzoylcarboxamido)phenoxyisobutyric acid;
4-(3,5-difluorophenylureido)phenoxyisobutyric acid;
4-(N-methyl-4-chlorobenzamido)phenoxyisobutyric acid;
4-(4-nitrophenylureido)phenoxyisobutyric acid;
4-(phenylureido)phenoxyacetic acid;
4-(4-chlorobenzoylcarboxamido)phenoxyisobutyric acid;
4-(2-hydroxy-4-chlorobenzoylcarboxamido) phenoxyisobutyric acid;
4-(2-hydroxy-3,5-dichlorobenzoylcarboxamido) phenoxyisobutyric acid;
4-(2-chloro-5-nitrophenylureido)phenoxyisobutyric acid;
4-carboxyphenoxyisobutyric acid;
4-(4-carboxyphenylureido)phenoxyisobutyric acid;
2-ureidophenoxyisobutyric acid;
urea 1,3-bis-4-phenoxyisobutyric acid;
4-(4-morpholinosulfonylphenylureido)phenoxyisobutyric acid;
4-[(3,4-dichlorophenylmethyl)2-chlorophenylureido] phenoxyisobutyric acid;
4-(3-pyridylureido)phenoxyisobutyric acid;
4-[(3,5-dichlorobenzoylamino)methyl]phenoxyisobutyric acid;
4-(2,4-dichlorophenacylamino)phenoxyisobutyric acid;
4-(benzylureido)phenoxyisobutyric acid;
4-acetamidobenzoic acid;
2-chloro-4-acetamidobenzoic acid;
4-aminophenoxyisobutyric acid;
2-acetamidoterephthalic acid;
5-chloro-2-acetoxybenzoic acid;
2-acetamido-5-acetoxybenzoic acid;
2-amino-5-hydroxybenzoic acid;
2-(8-quinolinoxy)propionic acid;
N-guanylguanidino-N'-4-phenoxyacetic acid;
2-(2,5-dichlorophenoxy)propionic acid;
4-dimethylaminobenzoic acid;
2-amino-4,5-dimethoxybenzoic acid;
4-sulfonamidobenzoic acid;
2-amino-4-chlorobenzoic acid;
4-hydroxyphenylbutyric acid;
2-methyl-4-quinolinecarboxylic acid;
2-methyl-3,4-quinolinedicarboxylic acid;
6-bromo-2-methyl-3,4-quinolinedicarboxylic acid;
4-acetamidophenoxyacetic acid;
1-(4-chlorophenoxybutyrylamido)-1-cyclohexanecarboxylic acid;
4-chlorophenylaminocarbonyliminodiacetic acid;
3-chloro-4-nitrophenylureidophenoxyisobutyric acid;
methylene bis [4,4'-(2-chlorophenylureidophenoxyisobutyric acid)];
N,N'-bis(2-chloro-4-carboxyphenyl)formamidine; and
N,N'-bis(2-carboxyphenyl)formamidine.

5. The method of claim 4 wherein said compound is selected from the group consisting of:
L-bis-[4-(4-chlorobenzamidophenoxyisobutyryl)cystine];
4-(3,5-dichlorophenylureido)phenoxyisobutyryl-1-amidocyclohexane-1-carboxylic acid;
4-(2-chloro-4-nitrophenylureido)phenoxyisobutyric acid;
4-(3-chloro-4-fluorophenylureido)phenoxyisobutyric acid;
4-(2,4-dichlorophenacylamino)phenoxyisobutyric acid; and
methylene bis [4,4'-(2-chlorophenylureidophenoxyisobutyric acid)].

6. The method of claim 4 wherein said compound is selected from the group consisting of:
4-(2,4,6-trichlorophenylureido)phenoxyisobutyric acid;
4-[(3,4-dichlorophenylmethyl)2-chlorophenylureido] phenoxyisobutyric acid; and
N,N'-bis(2-chloro-4-carboxyphenyl)formamidine.

7. A method of slowing progress in a patient of complications resulting from diabetes wherein said complications result from formation of glycation endproducts or protein crosslinking resulting from glycation, wherein said method comprises administering an effective amount of a compound or a pharmaceutically acceptable salt of said compound to said patient wherein said compound is selected from the group consisting of:

4-[3-(6-chloro-2,4-(1H, 3H) quinazolinedione)] phenoxyisobutyric acid;
4-(2-furoylcarboxamido)phenoxyisobutyric acid;
4-(3,5-dichlorophenylureido)phenoxyisobutyric acid;
4-(4-ethylcarbamatophenylureido)phenoxyisobutyric acid;
4-(3,4-dichlorophenylureido)phenoxyisobutyric acid;
4-cyclohexylureidophenoxyisobutyric acid;
4-(2,3-dichlorophenylureido)phenoxyisobutyric acid;
4-(4-carboxaldehydophenylureido)phenoxyisobutyric acid;
4-(2-naphthylcarboxamido)phenoxyisobutyric acid;
4-(4-methoxyphenylureido)phenoxyisobutyric acid;
4-(3,4-dimethoxyphenylureido)phenoxyisobutyric acid;
4-(4-chloro-3-nitrophenylureido)phenoxyisobutyric acid;
4-(4-methylphenylureido)phenoxyisobutyric acid;
4-(3,4,5-trimethoxyphenylureido)phenoxyisobutyric acid;
4-(3-chlorophenylureido)phenoxyisobutyric acid;
N-4-(nitrophthalimido)phenoxyisobutyric acid;
4-(2-thienylcarboxamido)phenoxyisobutyric acid;
4-(4-pyridylureido)phenoxyisobutyric acid;
4-(3,4,5-trichlorophenylureido)phenoxyisobutyric acid;
L-bis-[4-(4-chlorobenzamidophenoxyisobutyryl)cystine];
4-(3,4-dichlorophenylureido) phenoxyisobutamidomethylcyclohexyl-4-carboxylic acid;
DL-N-4-[(3,4-dichlorophenylureido)phenoxyisobutyryl] pipecolic acid;
4-(3,5-dichlorophenylureido)phenoxyisobutyryl-1-amidocyclohexane-1-carboxylic acid;
4-(4-iodophenylureido)phenoxyisobutyric acid;
4-(4-dimethylaminophenylureido)phenoxyisobutyric acid;
4-(2,4,6-trichlorophenylureido)phenoxyisobutyric acid;
4-(2,4,6-trimethylphenylureido)phenoxyisobutyric acid;
4-(4-chlorophenoxyacetamido)phenoxyisobutyric acid;
4-(4-chloro-3-nitrobenzoylcarboxamido) phenoxyisobutyric acid;
4-chlorodiphenylurea-4'-carboxylic acid;
4-(3,4-dichlorophenylacetamido)phenoxyisobutyric acid;
diphenylurea-4-carboxylic acid;
4-(2-chloro-4-nitrophenylureido)phenoxyisobutyric acid;
4-(nicotinylamido)phenoxyisobutyric acid;
4-chlorophenoxyisobutyric acid;
4-(benzylsulfonamido)phenoxyisobutyric acid;
4-(2,5-dichlorobenzoylcarboxamido)phenoxyisobutyric acid;
L-4-chlorobenzoylphenylalanine;
2-isopropyl-5-methylphenoxyisobutyric acid;
4-(3,4-dimethoxyphenylureido)phenoxyisobutyric acid;
4-(3-chloro-4-fluorophenylureido)phenoxyisobutyric acid;
4-(3,5-dichlorobenzamidoethyl)phenoxyisobutyric acid;
4-(phenylureido)phenoxyisobutyric acid;
4-(phenylureido-2-chloro)phenoxyisobutyric acid;
4-(2,6-dichloro-4-nitrobenzoylcarboxamido) phenoxyisobutyric acid;
4-(3,5-difluorophenylureido)phenoxyisobutyric acid;
4-(N-methyl-4-chlorobenzamido)phenoxyisobutyric acid;
4-(4-nitrophenylureido)phenoxyisobutyric acid;
4-(phenylureido)phenoxyacetic acid;
4-(4-chlorobenzoylcarboxamido)phenoxyisobutyric acid;
4-(2-hydroxy-4-chlorobenzoylcarboxamido) phenoxyisobutyric acid;
4-(2-hydroxy-3,5-dichlorobenzoylcarboxamido) phenoxyisobutyric acid;
4-(2-chloro-5-nitrophenylureido)phenoxyisobutyric acid;
4-carboxyphenoxyisobutyric acid;
4-(4-carboxyphenylureido)phenoxyisobutyric acid;
2-ureidophenoxyisobutyric acid;
urea 1,3-bis-4-phenoxyisobutyric acid;
4-(4-morpholinosulfonylphenylureido)phenoxyisobutyric acid;
4-[(3,4-dichlorophenylmethyl)2-chlorophenylureido] phenoxyisobutyric acid;
4-(3-pyridylureido)phenoxyisobutyric acid;
4-[(3,5-dichlorobenzoylamino)methyl]phenoxyisobutyric acid;
4-(2,4-dichlorophenacylamino)phenoxyisobutyric acid;
4-(benzylureido)phenoxyisobutyric acid;
4-acetamidobenzoic acid;
2-chloro-4-acetamidobenzoic acid;
4-aminophenoxyisobutyric acid;
2-acetamidoterephthalic acid;
5-chloro-2-acetoxybenzoic acid;
2-acetamido-5-acetoxybenzoic acid;
2-amino-5-hydroxybenzoic acid;
2-(8-quinolinoxy)propionic acid;
N-guanylguanidino-N'-4-phenoxyacetic acid;
2-(2,5-dichlorophenoxy)propionic acid;
4-dimethylaminobenzoic acid;
2-amino-4,5-dimethoxybenzoic acid;
4-sulfonamidobenzoic acid;
2-amino-4-chlorobenzoic acid;
4-hydroxyphenylbutyric acid;
2-methyl-4-quinolinecarboxylic acid;
2-methyl-3,4-quinolinedicarboxylic acid;
6-bromo-2-methyl-3,4-quinolinedicarboxylic acid;
4-acetamidophenoxyacetic acid;
1-(4-chlorophenoxybutyrylamido)-1-cyclohexanecarboxylic acid;
4-chlorophenylaminocarbonyliminodiacetic acid;
3-chloro-4-nitrophenylureidophenoxyisobutyric acid;
methylene bis [4,4'-(2-chlorophenylureidophenoxyisobutyric acid)];
N,N'-bis(2-chloro-4-carboxyphenyl)formamidine; and
N,N'-bis(2-carboxyphenyl)formamidine.

8. The method of claim 7 wherein said compound is selected from the group consisting of:
L-bis-[4-(4-chlorobenzamidophenoxyisobutyryl)cystine];

4-(3,5-dichlorophenylureido)phenoxyisobutyryl-1-amidocyclohexane-1-carboxylic acid;

4-(2-chloro-4-nitrophenylureido)phenoxyisobutyric acid;

4-(3-chloro-4-fluorophenylureido)phenoxyisobutyric acid;

4-(2,4-dichlorophenacylamino)phenoxyisobutyric acid; and methylene bis [4,4'-(2-chlorophenylureidophenoxyisobutyric acid)].

9. The method of claim 7 wherein said compound is selected from the group consisting of:

4-(2,4,6-trichlorophenylureido)phenoxyisobutyric acid;

4-[(3,4-dichlorophenylmethyl)2-chlorophenylureido]phenoxyisobutyric acid; and

N,N'-bis(2-chloro-4-carboxyphenyl)formamidine.

10. A method of slowing progress in a patient of rheumatoid arthritis, Alzheimer's disease, uremia, neurotoxicity, or atherosclerosis, wherein said method comprises administering an amount of a compound or a pharmaceutically acceptable salt of said compound to said patient wherein said amount is effective to inhibit formation of glycation endproducts or protein crosslinking resulting from glycation, wherein said compound is selected from the group consisting of:

4-[3-(6-chloro-2,4-(1H, 3H) quinazolinedione)]phenoxyisobutyric acid;

4-(2-furoylcarboxamido)phenoxyisobutyric acid;

4-(3,5-dichlorophenylureido)phenoxyisobutyric acid;

4-(4-ethylcarbamatophenylureido)phenoxyisobutyric acid;

4-(3,4-dichlorophenylureido)phenoxyisobutyric acid;

4-cyclohexylureidophenoxyisobutyric acid;

4-(2,3-dichlorophenylureido)phenoxyisobutyric acid;

4-(4-carboxaldehydophenylureido)phenoxyisobutyric acid;

4-(2-naphthylcarboxamido)phenoxyisobutyric acid;

4-(4-methoxyphenylureido)phenoxyisobutyric acid;

4-(3,4-dimethoxyphenylureido)phenoxyisobutyric acid;

4-(4-chloro-3-nitrophenylureido)phenoxyisobutyric acid;

4-(4-methylphenylureido)phenoxyisobutyric acid;

4-(3,4,5-trimethoxyphenylureido)phenoxyisobutyric acid;

4-(3-chlorophenylureido)phenoxyisobutyric acid;

N-4-(nitrophthalimido)phenoxyisobutyric acid;

4-(2-thienylcarboxamido)phenoxyisobutyric acid;

4-(4-pyridylureido)phenoxyisobutyric acid;

4-(3,4,5-trichlorophenylureido)phenoxyisobutyric acid;

L-bis-[4-(4-chlorobenzamidophenoxyisobutyryl)cystine];

4-(3,4-dichlorophenylureido)phenoxyisobutyrylamidomethylcyclohexyl-4-carboxylic acid;

DL-N4-[(3,4-dichlorophenylureido)phenoxyisobutyryl]pipecolic acid;

4-(3,5-dichlorophenylureido)phenoxyisobutyryl-1-amidocyclohexane-1-carboxylic acid;

4-(4-iodophenylureido)phenoxyisobutyric acid;

4-(4-dimethylaminophenylureido)phenoxyisobutyric acid;

4-(2,4,6-trichlorophenylureido)phenoxyisobutyric acid;

4-(2,4,6-trimethylphenylureido)phenoxyisobutyric acid;

4-(4-chlorophenoxyacetamido)phenoxyisobutyric acid;

4-(4-chloro-3-nitrobenzoylcarboxamido)phenoxyisobutyric acid;

4-chlorodiphenylurea-4'-carboxylic acid;

4-(3,4-dichlorophenylacetamido)phenoxyisobutyric acid;

diphenylurea-4-carboxylic acid;

4-(2-chloro-4-nitrophenylureido)phenoxyisobutyric acid;

4-(nicotinylamido)phenoxyisobutyric acid;

4-chlorophenoxyisobutyric acid;

4-(benzylsulfonamido)phenoxyisobutyric acid;

4-(2,5-dichlorobenzoylcarboxamido)phenoxyisobutyric acid;

L-4-chlorobenzoylphenylalanine;

2-isopropyl-5-methylphenoxyisobutyric acid;

4-(3,4-dimethoxyphenylureido)phenoxyisobutyric acid;

4-(3-chloro-4-fluorophenylureido)phenoxyisobutyric acid;

4-(3,5-dichlorobenzamidoethyl)phenoxyisobutyric acid;

4-(phenylureido)phenoxyisobutyric acid;

4-(phenylureido-2-chloro)phenoxyisobutyric acid;

4-(2,6-dichloro-4-nitrobenzoylcarboxamido)phenoxyisobutyric acid;

4-(3,5-difluorophenylureido)phenoxyisobutyric acid;

4-(N-methyl-4-chlorobenzamido)phenoxyisobutyric acid;

4-(4-nitrophenylureido)phenoxyisobutyric acid;

4-(phenylureido)phenoxyacetic acid;

4-(4-chlorobenzoylcarboxamido)phenoxyisobutyric acid;

4-(2-hydroxy-4-chlorobenzoylcarboxamido)phenoxyisobutyric acid;

4-(2-hydroxy-3,5-dichlorobenzoylcarboxamido)phenoxyisobutyric acid;

4-(2-chloro-5-nitrophenylureido)phenoxyisobutyric acid;

4-carboxyphenoxyisobutyric acid;

4-(4-carboxyphenylureido)phenoxyisobutyric acid;

2-ureidophenoxyisobutyric acid;

urea 1,3-bis-4-phenoxyisobutyric acid;

4-(4-morpholinosulfonylphenylureido)phenoxyisobutyric acid;

4-[(3,4-dichlorophenylmethyl)2-chlorophenylureido]phenoxyisobutyric acid;

4-(3-pyridylureido)phenoxyisobutyric acid;

4-[(3,5-dichlorobenzoylamino)methyl]phenoxyisobutyric acid;

4-(2,4-dichlorophenacylamino)phenoxyisobutyric acid;

4-(benzylureido)phenoxyisobutyric acid;

4-acetamidobenzoic acid;

2-chloro-4-acetamidobenzoic acid;

4-aminophenoxyisobutyric acid;

2-acetamidoterephthalic acid;

5-chloro-2-acetoxybenzoic acid;

2-acetamido-5-acetoxybenzoic acid;

2-amino-5-hydroxybenzoic acid;

2-(8-quinolinoxy)propionic acid;

N-guanylguanidino-N'-4-phenoxyacetic acid;

2-(2,5-dichlorophenoxy)propionic acid;

4-dimethylaminobenzoic acid;

2-amino-4,5-dimethoxybenzoic acid;

4-sulfonamidobenzoic acid;

2-amino-4-chlorobenzoic acid;
4-hydroxyphenylbutyric acid;
2-methyl-4-quinolinecarboxylic acid;
2-methyl -3,4-quinolinedicarboxylic acid;
6-bromo-2-methyl-3,4-quinolinedicarboxylic acid;
4-acetamidophenoxyacetic acid;
1-(4-chlorophenoxybutyrylamido)-1-cyclohexanecarboxylic acid;
4-chlorophenylaminocarbonyliminodiacetic acid;
3-chloro-4-nitrophenylureidophenoxyisobutyric acid;
methylene bis [4,4'-(2-chlorophenylureidophenoxyisobutyric acid)];
N,N'-bis(2-chloro-4-carboxyphenyl)formamidine; and
N,N'-bis(2-carboxyphenyl)fomamidine.

11. The method of claim 10 wherein said compound is selected from the group consisting of:
L-bis-[4-(4-chlorobenzamidophenoxyisobutyryl)cystine];
4-(3,5 -dichlorophenylureido)phenoxyisobutyryl-1-amidocyclohexane-1-carboxylic acid;
4-(2-chloro-4-nitrophenylureido)phenoxyisobutyric acid;
4-(3-chloro-4-fluorophenylureido)phenoxyisobutyric acid;
4-(2,4-dichlorophenacylarnino)phenoxyisobutyric acid; and
methylene bis [4,4'-(2-chlorophenylureidophenoxyisobutyric acid)].

12. The method of claim 10 wherein said compound is selected from the group consisting of:
4-(2,4,6-trichlorophenylureido)phenoxyisobutyric acid;
4-[(3,4-dichlorophenylmethyl)2-chlorophenylureido]phenoxyisobutyric acid; and
N,N'-bis(2-chloro-4-carboxyphenyl)formamidine.

13. A method of preventing browning or Maillard reaction in foodstuffs wherein said method comprises mixing an effective amount of a compound or a pharmaceutically acceptable salt of said compound with said foodstuffs, wherein said effective amount inhibits formation of glycation endproducts or protein crosslinking resulting from glycation, wherein said compound is selected from the group consisting of:
4-[3-(6-chloro-2,4-(1H, 3H) quinazolinedione)] phenoxyisobutyric acid;
4-(2-furoylcarboxamido)phenoxyisobutyric acid;
4-(3,5-dichlorophenylureido)phenoxyisobutyric acid;
4-(4-ethylcarbamatophenylureido)phenoxyisobutyric acid;
4-(3,4-dichlorophenylureido)phenoxyisobutyric acid;
4-cyclohexylureidophenoxyisobutyric acid;
4-(2,3-dichlorophenylureido)phenoxyisobutyric acid;
4-(4-carboxaldehydophenylureido)phenoxyisobutyric acid;
4-(2-naphthylcarboxamido)phenoxyisobutyric acid;
4-(4-methoxyphenylureido)phenoxyisobutyric acid;
4-(3,4-dimethoxyphenylureido)phenoxyisobutyric acid;
4-(4-chloro-3-nitrophenylureido)phenoxyisobutyric acid;
4-(4-methylphenylureido)phenoxyisobutyric acid;
4-(3,4,5-trimethoxyphenylureido)phenoxyisobutyric acid;
4-(3-chlorophenylureido)phenoxyisobutyric acid;
N-4-(nitrophthalimido)phenoxyisobutyric acid;
4-(2-thienylcarboxamido)phenoxyisobutyric acid;
4-(4-pyridylureido)phenoxyisobutyric acid;
4-(3,4,5-trichlorophenylureido)phenoxyisobutyric acid;
L-bis-[4-(4-chlorobenzamidophenoxyisobutyryl)cystine];
4-(3,4-dichlorophenylureido)phenoxyisobutyrylamidomethylcyclohexyl-4-carboxylic acid;
DL-N-4-[(3,4-dichlorophenylureido)phenoxyisobutyryl] pipecolic acid;
4-(3,5-dichlorophenylureido)phenoxyisobutyryl-1-amidocyclohexane-1-carboxylic acid;
4-(4-iodophenylureido)phenoxyisobutyric acid;
4-(4-dimethylaminophenylureido)phenoxyisobutyric acid;
4-(2,4,6-trichlorophenylureido)phenoxyisobutyric acid;
4-(2,4,6-trimethylphenylureido)phenoxyisobutyric acid;
4-(4-chlorophenoxyacetamido)phenoxyisobutyric acid;
4-(4-chloro-3-nitrobenzoylcarboxamido) phenoxyisobutyric acid;
4-chlorodiphenylurea-4'-carboxylic acid;
4-(3,4-dichlorophenylacetamido)phenoxyisobutyric acid;
diphenylurea-4-carboxylic acid;
4-(2-chloro-4-nitrophenylureido)phenoxyisobutyric acid;
4-(nicotinylamido)phenoxyisobutyric acid;
4-chlorophenoxyisobutyric acid;
4-(benzylsulfonamido)phenoxyisobutyric acid;
4-(2,5-dichlorobenzoylcarboxamido)phenoxyisobutyric acid;
L-4-chlorobenzoylphenylalanine;
2-isopropyl-5-methylphenoxyisobutyric acid;
4-(3,4-dimethoxyphenylureido)phenoxyisobutyric acid;
4-(3-chloro-4-fluorophenylureido)phenoxyisobutyric acid;
4-(3,5-dichlorobenzamidoethyl)phenoxyisobutyric acid;
4-(phenylureido)phenoxyisobutyric acid;
4-(phenylureido-2-chloro)phenoxyisobutyric acid;
4-(2,6-dichloro-4-nitrobenzoylcarboxamido) phenoxyisobutyric acid;
4-(3,5-difluorophenylureido)phenoxyisobutyric acid;
4-(N-methyl-4-chlorobenzamido)phenoxyisobutyric acid;
4-(4-nitrophenylureido)phenoxyisobutyric acid;
4-(phenylureido)phenoxyacetic acid;
4-(4-chlorobenzoylcarboxamido)phenoxyisobutyric acid;
4-(2-hydroxy-4-chlorobenzoylcarboxamido) phenoxyisobutyric acid;
4-(2-hydroxy-3,5-dichlorobenzoylcarboxamido) phenoxyisobutyric acid;
4-(2-chloro-5-nitrophenylureido)phenoxyisobutyric acid;
4-carboxyphenoxyisobutyric acid;
4-(4-carboxyphenylureido)phenoxyisobutyric acid;
2-ureidophenoxyisobutyric acid;
urea 1,3-bis-4-phenoxyisobutyric acid;
4-(4-morpholinosulfonylphenylureido)phenoxyisobutyric acid;
4-[(3,4-dichlorophenylmethyl)2-chlorophenylureido] phenoxyisobutyric acid;
4-(3-pyridylureido)phenoxyisobutyric acid;
4-[(3,5-dichlorobenzoylarnino)methyl] phenoxyisobutyric acid;

4-(2,4-dichlorophenacylamino)phenoxyisobutyric acid;
4-(benzylureido)phenoxyisobutyric acid;
4-acetamidobenzoic acid;
2-chloro-4-acetamidobenzoic acid;
4-aminophenoxyisobutyric acid;
2-acetamidoterephthalic acid;
5-chloro-2-acetoxybenzoic acid;
2-acetamido-5-acetoxybenzoic acid;
2-amino-5-hydroxybenzoic acid;
2-(8-quinolinoxy)propionic acid;
N-guanylguanidino-N'-4-phenoxyacetic acid;
2-(2,5-dichlorophenoxy)propionic acid;
4-dimethylaminobenzoic acid;
2-amino-4,5-dimethoxybenzoic acid;
4-sulfonamidobenzoic acid;
2-amino-4-chlorobenzoic acid;
4-hydroxyphenylbutyric acid;
2-methyl-4-quinolinecarboxylic acid;
2-methyl-3,4-quinolinedicarboxylic acid;
6-bromo-2-methyl-3,4-quinolinedicarboxylic acid;
4-acetamidophenoxyacetic acid;
1-(4-chlorophenoxybutyrylamido)-1-cyclohexanecarboxylic acid;
4-chlorophenylaminocarbonyliminodiacetic acid;
3-chloro-4-nitrophenylureidophenoxyisobutyric acid;
methylene bis [4,4'-(2-chlorophenylureidophenoxyisobutyric acid)];
N,N'-bis(2-chloro-4-carboxyphenyl)formamidine; and
N,N'-bis(2-carboxyphenyl)formamidine.

14. The method of claim 13 wherein said compound is selected from the group consisting of:
L-bis-[4-(4-chlorobenzamidophenoxyisobutyryl)cystine];
4-(3,5-dichlorophenylureido)phenoxyisobutyryl-1-amidocyclohexane-1-carboxylic acid;
4-(2-chloro-4-nitrophenylureido)phenoxyisobutyric acid;
4-(3-chloro-4-fluorophenylureido)phenoxyisobutyric acid;
4-(2,4-dichlorophenacylamino)phenoxyisobutyric acid; and
methylene bis [4,4'-(2-chlorophenylureidophenoxyisobutyric acid)].

15. The method of claim 13 wherein said compound is selected from the group consisting of:
4-(2,4,6-trichlorophenylureido)phenoxyisobutyric acid;
4-[(3,4-dichlorophenylmethyl)2-chlorophenylureido]phenoxyisobutyric acid; and
N,N'-bis(2-chloro-4-carboxyphenyl)formamidine.

16. A compound or a pharmaceutically acceptable salt of said compound wherein said compound is selected from the group consisting of:
L-bis-[4-(4-chlorobenzamidophenoxyisobutyryl)cystine];
4-(3,5-dichlorophenylureido)phenoxyisobutyryl-1-amidocyclohexane-1-carboxylic acid;
4-(2-chloro-4-nitrophenylureido)phenoxyisobutyric acid;
4-[(3,4-dichlorophenylmethyl)2-chlorophenylureido]phenoxyisobutyric acid;
4-(2,4-dichlorophenacylamino)phenoxyisobutyric acid; and
N,N'-bis(2-chloro-4-carboxyphenyl)foramidine .

17. A pharmaceutical composition comprising an effective amount of a compound or a pharmaceutically acceptable salt of said compound and a pharmaceutical carrier wherein said compound is a compound of claim 16.

18. A method of inhibiting formation of glycation endproducts or protein crosslinking resulting from glycation in a mammal in which it is desired to inhibit formation of glycation endproducts or protein crosslinking, wherein said method comprises administering an amount of a compound or a pharmaceutically acceptable salt of said compound to said mammal wherein said amount is effective in inhibiting formation of glycation endproducts or protein crosslinking, wherein said compound is:

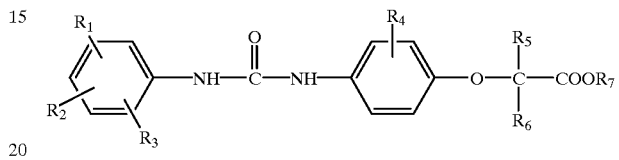

wherein $R_1$, $R_2$, $R_3$ and $R_4$ may be the same or different and are independently selected from the group consisting of hydrogen, halogen, straight or branched chain alkyl of from 1–6 carbon atoms, aryl, cycloalkyl of 3 to 7 carbon atoms, and alkoxy of 1 to 6 carbon atoms; $R_5$ and $R_6$ may be the same or different and are selected from the group consisting of hydrogen, halogen, straight or branched chain alkyl groups of from 1 to 6 carbon atoms, aralkyl wherein the alkyl portion has from 1 to 6 carbon atoms, cycloalkyl of from 3 to 7 carbon atoms and aryl; and $R_7$ is hydrogen or a straight or branched chain alkyl group of 1 to 6 carbon atoms and the pharmaceutically acceptable salts thereof.

19. A method of slowing deleterious effects of aging in a mammal in which it is desired to slow the deleterious effects of aging wherein said effects are formation of glycation endproducts or protein crosslinking resulting from glycation, wherein said method comprises administering an amount of a compound or a pharmaceutically acceptable salt of said compound to said mammal wherein said amount is effective to inhibit formation of glycation endproducts or protein crosslinking, wherein said compound is:

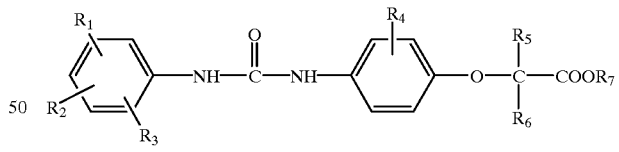

wherein $R_1$, $R_2$, $R_3$ and $R_4$ may be the same or different and are independently selected from the group consisting of hydrogen, halogen, straight or branched chain alkyl of from 1–6 carbon atoms, aryl, cycloalkyl of 3 to 7 carbon atoms, and alkoxy of 1 to 6 carbon atoms;

$R_5$ and $R_6$ may be the same or different and are selected from the group consisting of hydrogen, halogen, straight or branched chain alkyl groups of from 1 to 6 carbon atoms, aralkyl wherein the alkyl portion has from 1 to 6 carbon atoms, cycloalkyl of from 3 to 7 carbon atoms and aryl; and $R_7$ is hydrogen or a straight or branched chain alkyl group of 1 to 6 carbon atoms and the pharmaceutically acceptable salts thereof.

20. A method of slowing progress in a patient of complications resulting from diabetes wherein said complications result from formation of glycation endproducts or protein crosslinking resulting from glycation, wherein said method comprises administering an effective amount of a compound or a pharmaceutically acceptable salt of said compound to said patient wherein said compound is:

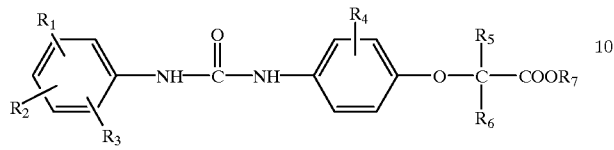

wherein $R_1$, $R_2$, $R_3$ and $R_4$ may be the same or different and are independently selected from the group consisting of hydrogen, halogen, straight or branched chain alkyl of from 1–6 carbon atoms, aryl, cycloalkyl of 3 to 7 carbon atoms, and alkoxy of 1 to 6 carbon atoms;

$R_5$ and $R_6$ may be the same or different and are selected from the group consisting of hydrogen, halogen, straight or branched chain alkyl groups of from 1 to 6 carbon atoms, aralkyl wherein the alkyl portion has from 1 to 6 carbon atoms, cycloalkyl of from 3 to 7 carbon atoms and aryl; and $R_7$ is hydrogen or a straight or branched chain alkyl group of 1 to 6 carbon atoms and the pharmaceutically acceptable salts thereof.

21. A method of slowing progress in a patient of rheumatoid arthritis, Alzheimer's disease, uremia, neurotoxicity, or atherosclerosis, wherein said method comprises administering an amount of a compound or a pharmaceutically acceptable salt of said compound to said patient wherein said amount is effective to inhibit formation of glycation endproducts or protein crosslinking resulting from glycation, wherein said compound is:

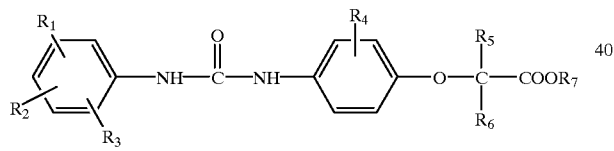

wherein $R_1$, $R_2$, $R_3$ and $R_4$ may be the same or different and are independently selected from the group consisting of hydrogen, halogen, straight or branched chain alkyl of from 1–6 carbon atoms, aryl, cycloalkyl of 3 to 7 carbon atoms, and alkoxy of 1 to 6 carbon atoms;

$R_5$ and $R_6$ may be the same or different and are selected from the group consisting of hydrogen, halogen, straight or branched chain alkyl groups of from 1 to 6 carbon atoms, aralkyl wherein the alkyl portion has from 1 to 6 carbon atoms, cycloalkyl of from 3 to 7 carbon atoms and aryl; and $R_7$ is hydrogen or a straight or branched chain alkyl group of 1 to 6 carbon atoms and the pharmaceutically acceptable salts thereof.

22. A method of preventing browning or Maillard reaction in foodstuffs wherein said method comprises mixing an effective amount of a compound or a pharmaceutically acceptable salt of said compound with said foodstuffs, wherein said effective amount inhibits formation of glycation endproducts or protein crosslinking resulting from glycation, wherein said compound is:

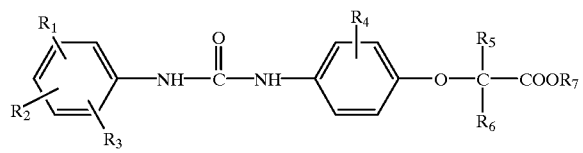

wherein $R_1$, $R_2$, $R_3$ and $R_4$ may be the same or different and are independently selected from the group consisting of hydrogen, halogen, straight or branched chain alkyl of from 1–6 carbon atoms, aryl, cycloalkyl of 3 to 7 carbon atoms, and alkoxy of 1 to 6 carbon atoms;

$R_5$ and $R_6$ may be the same or different and are selected from the group consisting of hydrogen, halogen, straight or branched chain alkyl groups of from 1 to 6 carbon atoms, aralkyl wherein the alkyl portion has from 1 to 6 carbon atoms, cycloalkyl of from 3 to 7 carbon atoms and aryl; and $R_7$ is hydrogen or a straight or branched chain alkyl group of 1 to 6 carbon atoms and the pharmaceutically acceptable salts thereof.

* * * * *

UNITED STATES PATENT AND TRADEMARK OFFICE
CERTIFICATE OF CORRECTION

PATENT NO. : 6,337,350 B1
DATED : January 8, 2002
INVENTOR(S) : Samuel Rahbar and Iraj Lalezari It is certified that error appears in the above-identified patent and that said Letters Patent is hereby corrected as shown below:

Column 12,
Line 43, in Example 3, replace "(Coming)" with -- (Corning) --.

Column 17,
Line 30, replace "nitrobenzoylcarboxarnido" with -- nitrobenzoylcarboxamido --.

Column 19,
Lines 30 and 40, replace "nitrobenzoylcarboxarnido" with
-- nitrobenzoylcarboxamido --.

Column 21,
Line 35, replace "phenoxyrsobutamidomethylcyclohexyl" with
-- phenoxyisobutyrylamidomethylcyclohexyl --.

Column 24,
Line 1, replace "nitrobenzoylcarboxarnido" with -- nitrobenzoylcarboxamido --.

Column 26,
Line 66, replace "dichlorobenzoylarnio" with -- dichlorobenzoylamino --.

Signed and Sealed this

Twenty-fifth Day of May, 2004

JON W. DUDAS
*Acting Director of the United States Patent and Trademark Office*